United States Patent
Yori et al.

(10) Patent No.: US 11,261,412 B2
(45) Date of Patent: Mar. 1, 2022

(54) LIQUID TRANSPORT METHOD

(71) Applicant: TERUMO KABUSHIKI KAISHA, Tokyo (JP)

(72) Inventors: Kouichirou Yori, Kanagawa (JP); Makoto Jinno, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/863,327

(22) Filed: Apr. 30, 2020

(65) Prior Publication Data

US 2020/0255779 A1    Aug. 13, 2020

Related U.S. Application Data

(63) Continuation of application No. 15/632,937, filed on Jun. 26, 2017, now Pat. No. 10,787,633, which is a
(Continued)

(30) Foreign Application Priority Data

Dec. 26, 2014 (JP) ................................. 2014-265891

(51) Int. Cl.
*C12M 1/10* (2006.01)
*B25J 9/16* (2006.01)
(Continued)

(52) U.S. Cl.
CPC .............. *C12M 1/10* (2013.01); *B25J 9/042* (2013.01); *B25J 9/10* (2013.01); *B25J 9/1612* (2013.01);
(Continued)

(58) Field of Classification Search
CPC . C12M 1/10; C12M 1/00; C12M 41/48; B25J 9/042; B25J 9/10; B25J 9/1612;
(Continued)

(56) References Cited

U.S. PATENT DOCUMENTS 3,943,992 A    3/1976 Mezger
4,134,444 A    1/1979 Fujie et al.
(Continued)

FOREIGN PATENT DOCUMENTS

CA    2274226 A1    1/2000
JP    H03007838 A    1/1991
(Continued)

OTHER PUBLICATIONS

Office Action (Notice of Reasons for Refusal) dated Jul. 29, 2019, by the Japanese Patent Office in corresponding Japanese Patent Application No. 2016-566482 and an English Translation of the Office Action. (5 pages).
(Continued)

*Primary Examiner* — Glenn F Myers
(74) *Attorney, Agent, or Firm* — Buchanan Ingersoll & Rooney PC

(57) ABSTRACT

A liquid transport method is disclosed for efficiently producing cell cultures. The liquid transport method of the present disclosure, which is in processing of cells, includes: a) a step in which a container holding a liquid is gripped by a gripping tool of a robot; and b) a step in which the liquid in the container is transported to a collection container by rotating the gripped container. In steps a) and b) the robot operates such as not to pass over a vertical line of an opening of the collection container.

16 Claims, 19 Drawing Sheets

Related U.S. Application Data continuation of application No. PCT/JP2015/086158, filed on Dec. 25, 2015.

(51) Int. Cl.

| | | |
|---|---|---|
| *B25J 9/04* | (2006.01) | |
| *B25J 9/10* | (2006.01) | |
| *B25J 21/00* | (2006.01) | |
| *B25J 21/02* | (2006.01) | |
| *C12M 1/36* | (2006.01) | |
| *G01N 35/10* | (2006.01) | |
| *C12M 1/00* | (2006.01) | |
| *G01N 35/00* | (2006.01) | |

(52) U.S. Cl.
CPC ........... *B25J 9/1676* (2013.01); *B25J 9/1679* (2013.01); *B25J 21/00* (2013.01); *B25J 21/02* (2013.01); *C12M 41/48* (2013.01); *G01N 35/1009* (2013.01); *G01N 35/1016* (2013.01); *C12M 1/00* (2013.01); *G01N 35/0099* (2013.01); *G05B 2219/40073* (2013.01)

(58) Field of Classification Search
CPC ........ B25J 9/1676; B25J 9/1679; B25J 21/00; B25J 21/02; G01N 35/1009; G01N 35/1016; G01N 35/0099; G05B 2219/40073

See application file for complete search history.

(56) References Cited

U.S. PATENT DOCUMENTS

| | | | |
|---|---|---|---|
| 4,210,192 A | 7/1980 | Lavanchy et al. | |
| 4,313,707 A | 2/1982 | Bingman et al. | |
| 6,604,903 B2 | 8/2003 | Osborne et al. | |
| 7,022,151 B2 | 4/2006 | Ono | |
| 9,439,361 B2 | 9/2016 | Teasdale | |
| 9,789,986 B2 | 10/2017 | Procyshyn et al. | |
| 2001/0003931 A1 | 6/2001 | Suzuki et al. | |
| 2006/0043111 A1* | 3/2006 | Jennings | B25J 9/0087 222/129.1 |
| 2006/0115889 A1 | 6/2006 | Nakashima et al. | |
| 2007/0092492 A1 | 4/2007 | Matsuda et al. | |
| 2007/0238173 A1 | 10/2007 | Yamagami et al. | |
| 2008/0142743 A1 | 6/2008 | Tartaglia | |
| 2008/0247914 A1 | 10/2008 | Edens et al. | |
| 2009/0053277 A1 | 2/2009 | Nagaya et al. | |
| 2010/0126286 A1 | 5/2010 | Self et al. | |
| 2013/0252533 A1* | 9/2013 | Mauck | F24F 3/14 454/187 |
| 2014/0106386 A1* | 4/2014 | Umeno | B25J 9/0087 435/23 |
| 2015/0166208 A1 | 6/2015 | Miyauchi | |

FOREIGN PATENT DOCUMENTS

| | | |
|---|---|---|
| JP | H11243948 A | 9/1999 |
| JP | 2002262856 A | 9/2002 |
| JP | 2002267666 A | 9/2002 |
| JP | 2005229869 A | 9/2005 |
| JP | 2006149268 A | 6/2006 |
| JP | 2007528755 A | 10/2007 |
| JP | 2008-239168 A | 10/2008 |
| JP | 2010081829 A | 4/2010 |
| JP | 2010226991 A | 10/2010 |
| JP | 2011-167405 A | 9/2011 |
| JP | 2012029691 A | 2/2012 |
| JP | 2012152154 A | 8/2012 |
| JP | 2013009618 A | 1/2013 |
| WO | 2006080434 A1 | 8/2006 |

OTHER PUBLICATIONS

K. Ohashi et al., "Production of Islet Cell Sheets Using Cryopreserved Islet Cells", Transplantation Proceedings, 2011, pp. 3188-3191.

International Search Report (PCT/ISA/210) dated Apr. 5, 2016, by the Japanese Patent Office as the International Searching Authority for International Application No. PCT/JP2015/086158.

Yuji Haraguchi et al., "Concise Review: Cell Therapy and Tissue Engineering for Cardiovascular Disease", Stem Cells Translational Medicine, 2012, pp. 136-141.

Office Action (Notice of Reasons for Refusal) dated Sep. 2, 2021, by the Japanese Patent Office in corresponding Japanese Patent Application No. 2020-095708 and an English Translation of the Office Action. (7 pages).

* cited by examiner

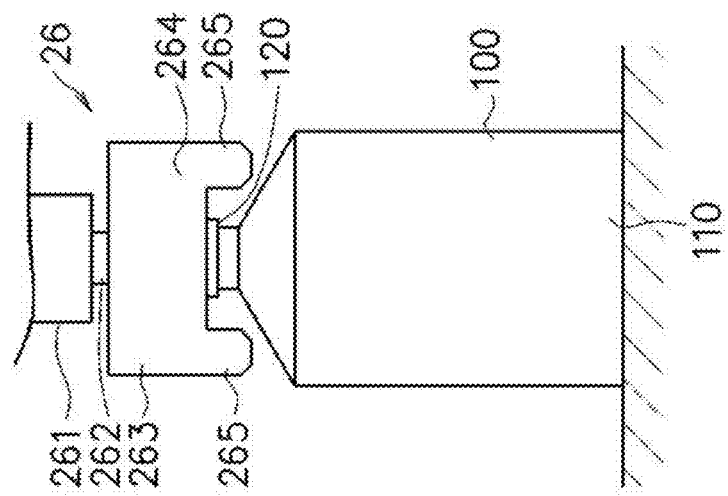
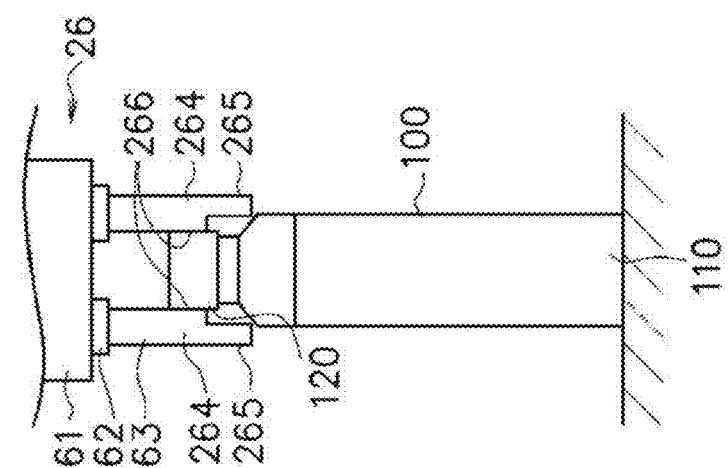
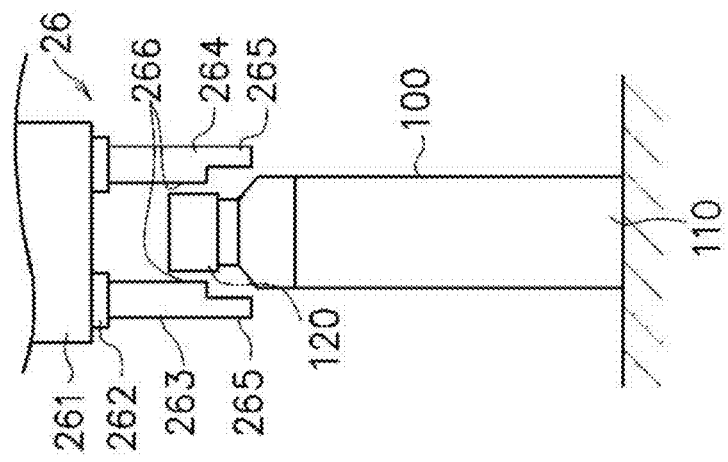

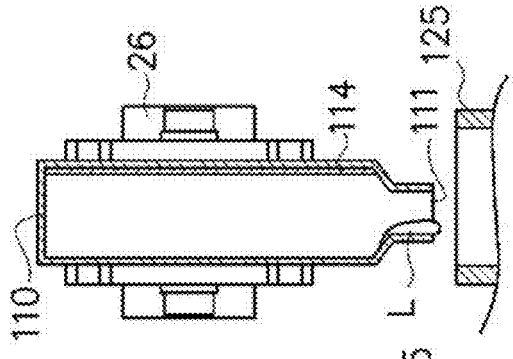
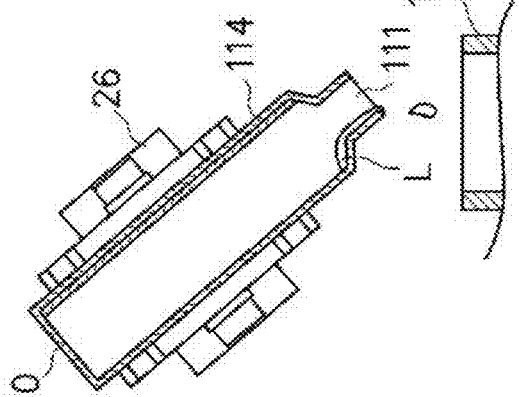
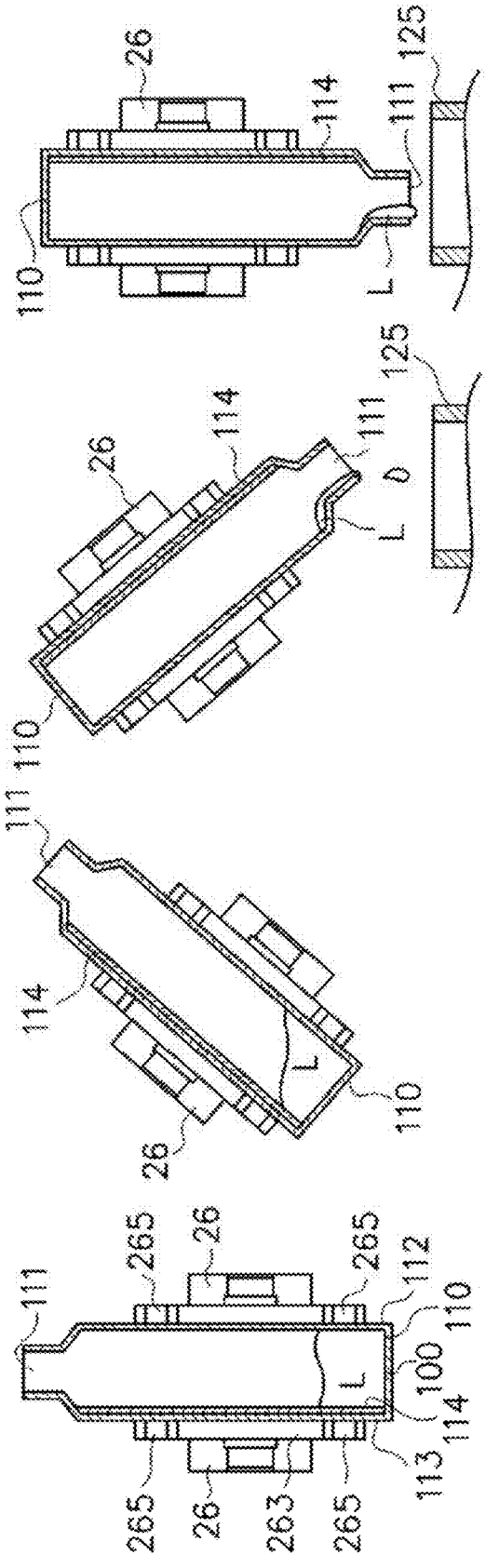
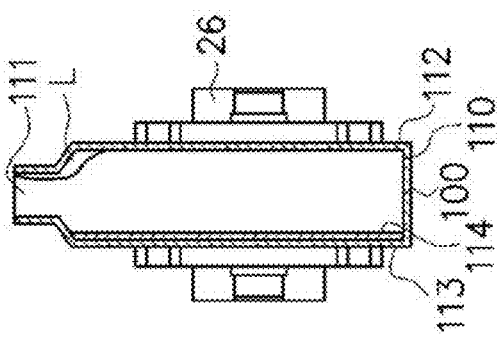
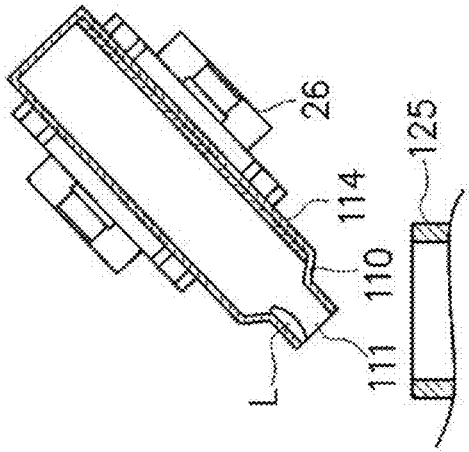

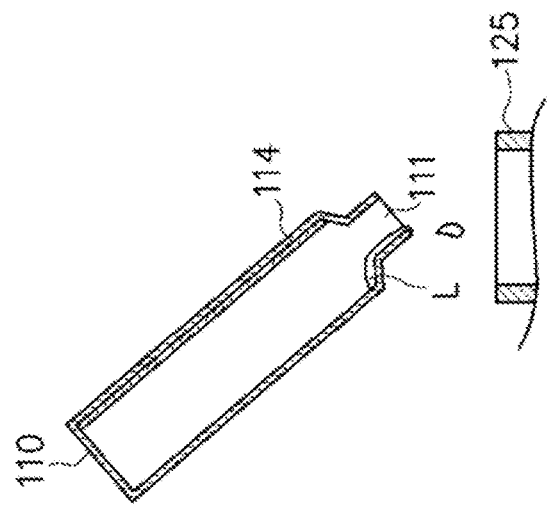
FIG. 13 (a)
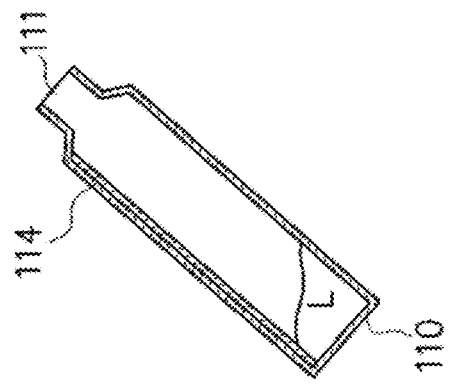
FIG. 13 (b)
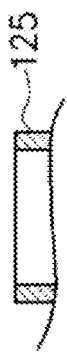
FIG. 13 (c)
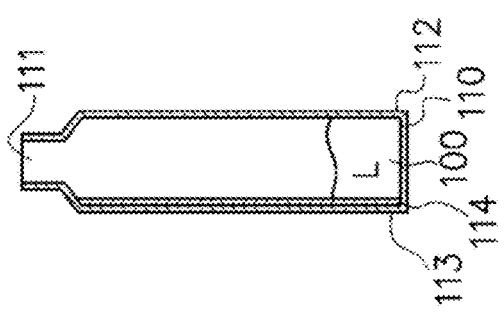
FIG. 13 (d)
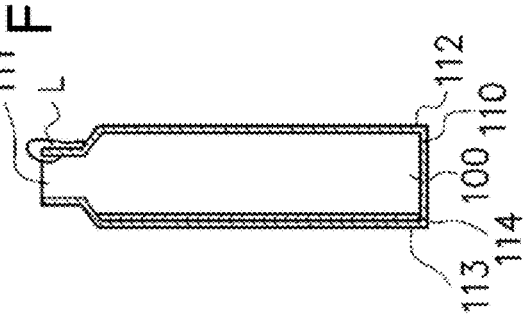
FIG. 13 (e)
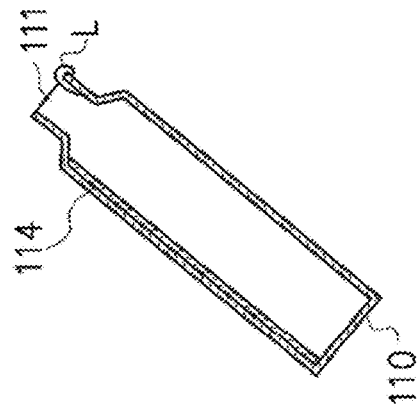

LIQUID TRANSPORT METHOD

CROSS-REFERENCES TO RELATED APPLICATIONS

This application is a continuation of U.S. application Ser. No. 15/632,937, filed on Jun. 26, 2017, which is a continuation of International Application No. PCT/JP2015/086158, filed on Dec. 25, 2015, which claims priority to Japanese Patent Application No. 2014-265891, filed on Dec. 26, 2014, the entire content of all three of which is incorporated herein by reference.

TECHNICAL FIELD

The present disclosure relates to a liquid transport method, a cell processing system, and a cell processing method.

BACKGROUND DISCUSSION

In recent years, various attempts to transplant cells have been made for repair of injured tissues and the like. For example, for repair of myocardial tissues injured due to ischemic heart diseases such as angina pectoris and myocardial infarction, utilization of fetal myocardial cells, skeletal myoblasts, mesenchymal stem cells, cardiac stem cells, embryo-stem (ES) cells, etc. has been attempted (See Haraguchi et al., Stem Cells Transl Med. 2012 February; 1(2): 136-41).

In connection with such attempts, cell structures formed utilizing a scaffold and sheet-shaped cell cultures obtained by forming cells into a sheet-shaped form have been developed (See JP2007528755(A), PCT Patent Publication No. WO2006/080434, JP2005229869(A), JP201081829(A), JP2010226991(A), and JP2006149268(A), and Ohashi et al., Transplant Proc. 2011 November; 43(9): 3188-91).

In regard of application of sheet-shaped cell cultures to therapy, investigations have been made as to utilization of cultured skin sheets for skin injury due to burn or the like, utilization of corneal epithelium sheet-shaped cell cultures for corneal injury, utilization of mouth mucosa sheet-shaped cell cultures for endoscopic resection of esophageal carcinoma, etc.

However, such sheet-shaped cell cultures and cell structures must be produced in clean environments, and high levels of knowledge and skill are required for the production thereof. For this reason, in the past, these cell cultures have been manually produced in a clean room called a cell processing center (CPC) by an operator having expert knowledge. Thus, huge cost and labor have been required for the production of such cell cultures.

In view of this, an automatic cell culture apparatus for performing the operations concerning culture of the cells by an articulated robot is disclosed.

SUMMARY

During various studies conducted in this technical field by the present inventors, attention was paid to the problem that in the case of automatically performing all the operations concerning cell culture by a robot, the configuration of the apparatus is complicated, with the result that maintainability and system extensibility would be relatively poor, and efficient use would be virtually impossible. A system is disclosed in which a combination of robot operations and manual operations can be performed in an integrated manner, which is capable of more rationally contributing to the cell culture technology, rather than a method of performing all the operations by depending on a robot or robots.

Accordingly, a cell processing system is disclosed which enables efficient production of cell cultures through a rational combination of robot operations and manual operations and has a comparatively simple configuration, and a cell processing method, a liquid transport method, and a gripping tool which are for efficient production of cell cultures.

The aforesaid object, which can be achieved by a rational combination of robot operations and manual operations, is achieved by, for example, the following means (1) to (30).

(1) A cell processing system, which is a system for use in processing of cells by use of a container, the cell processing system includes: a base provided with a plurality of processing areas for performing processing by use of the container and a carrying-in/carrying-out area where things for use in the processing can be carried in and carried out; a robot that is provided on the base and has a gripping tool capable of gripping at least part of the container; a housing that covers the processing areas, the robot, and at least part of the carrying-in/carrying-out area and is able to maintain cleanliness of inside thereof; and at least one working section that is disposed on the housing or the base and is configured in such a manner that manual operation in the housing from outside of the housing can be performed thereby, wherein the gripping tool of the robot can reach the processing areas, the housing is configured such that its part adjacent to the carrying-in/carrying-out area can be opened and closed, and the working section is configured such that its workable area overlaps with the processing area and/or the carrying-in/carrying-out area, and things for use in the processing can be moved between the respective processing areas and the carrying-in/carrying-out area through the working section.

(2) The cell processing system as described in (1), includes a plurality of the working sections, wherein workable areas of the working sections adjacent to each other overlap with each other.

(3) The cell processing system as described in (1) or (2), wherein manual preparation for the processing in the processing area can be performed by the working section.

(4) The cell processing system as described in any one of (1) to (3), wherein the processing is performed by the robot.

(5) The cell processing system as described in any one of (1) to (4), wherein the working section is a glove.

(6) The cell processing system as described in any one of (1) to (5), wherein at least one of the processing area is an area for dispensing a liquid into the container.

(7) The cell processing system as described in any one of (1) to (6), wherein at least one of the processing areas is an area for disposing of the liquid in the container.

(8) The cell processing system as described in (6) or (7), wherein the liquid is a culture medium.

(9) The cell processing system as described in any one of (1) to (8), wherein the container includes a container main body and a cap, and at least one of the processing areas is an area for attachment and detachment of the cap to and from the container main body.

(10) The cell processing system as described in any one of (1) to (9), wherein the system uses for exchange of a culture medium in the container, dispensing of the culture medium into the container, inoculation of cells into the container, and/or dissection of a cell tissue formed on an inner wall surface of the container.

(11) A cell processing system, which is a system for use in processing of cells by use of a container, the cell processing system includes: a base provided with at least one processing area for performing the processing by use of the container and a container carrying-in/carrying-out area; a robot that is provided on the base and has a gripping tool capable of gripping at least part of the container; and a housing that covers at least the processing areas and the robot and is able to maintain cleanliness of inside thereof, wherein the gripping tool of the robot can reach the processing areas, the gripping tool includes a first gripping section, and a second gripping section that is disposed on a distal tip side relative to the first gripping section and is larger than the first gripping section in separated distance between gripping surfaces, and the second gripping section has a configuration in which part thereof is omitted in a vicinity of a center axis of the first gripping section.

(12) A gripping tool for a robot that is used in operating a container for processing cells, the gripping tool includes: a first gripping section; and a second gripping section that is disposed on a distal tip side relative to the first gripping section and is larger than the first gripping section in separated distance between gripping surfaces, wherein the second gripping section has a configuration in which part thereof is omitted in a vicinity of a center axis of the first gripping section.

(13) The gripping tool as described in (12), wherein the second gripping section is disposed at a position corresponding to an end portion on a lateral side of the gripping surface of the first gripping section.

(14) The gripping tool as described in (12) or (13), wherein the second gripping section is disposed at a position corresponding to both end portions on lateral sides of the gripping surfaces of the first gripping section.

(15) The gripping tool as described in any one of (12) to (14), wherein the first gripping section has a recessed part in a vicinity of a center of the gripping surface, along an axial direction.

(16) The gripping tool as described in any one of (12) to (15), wherein anti-slipping portions are disposed on the gripping surfaces of the first gripping section and/or the second gripping section.

(17) A cell processing method for processing cells by use of a plurality of containers each having a cap and a container main body, the cell processing method includes:

1) a step of disposing n (where n is an integer of not less than 2) containers to be processed in a predetermined order;

2) a step of detaching the cap from the container main body of the container to be processed i-thly (where i is an integer satisfying 2≤i≤n) and attaching the cap to the container main body of the container processed (i−1) thly, by a robot; and 3) a step of performing the processing by use of the container to be processed i-thly.

(18) The cell processing method as described in (17), wherein step 2) and step 3) are repeated until i increases from 2 to n.

(19) The cell processing method as described in (17) or (18), wherein the robot operates in such a manner as not to pass over an opening of the container main body from which the cap has been detached.

(20) The cell processing method as described in any one of (17) to (19), includes, prior to step 2), a step of detaching the cap of the container to be processed i-thly from the container main body by the robot and disposing the cap on a cap depository.

(21) The cell processing method as described in any one of (17) to (20), wherein after the processing of step 3) is conducted for the container to be processed n-thly, the cap disposed on the cap depository is attached to the container main body of the container by the robot.

(22) The cell processing method as described in any one of (17) to (21), wherein the processing in step 3) is disposal of a liquid from the container and/or pouring of a liquid into the container.

(23) The cell processing method as described in (22), wherein the liquid is a culture medium.

(24) The cell processing method as described in any one of (17) to (23), wherein the processing is exchange of a culture medium in the container, dispensing of a culture medium into the container, inoculation of cells into the container, or dissection of a cell tissue formed on an inner wall surface of the container.

(25) A liquid transport method in processing of cells, the liquid transport method includes:

a) a step in which a container holding a liquid is gripped by a gripping tool of a robot; and b) a step in which the liquid in the container is transported to a collection container by rotating the gripped container, wherein in steps a) and b), the robot operates in such a manner as not to pass over a vertical line of an opening of the collection container.

(26) The liquid transport method as described in (25), wherein the gripping tool is rotatable, and in step b), the container is rotated, in the same direction, about a center axis consisting of an axis parallel to an axis of rotation of the gripping tool.

(27) The liquid transport method as described in (25) or (26), wherein in step b), the container is reciprocated up and down when the opening of the container is oriented downward.

(28) The liquid transport method as described in any one of (25) to (27), wherein in step b), the rotation of the container is performed while being accompanied by a translational motion.

(29) The liquid transport method as described in any one of (25) to (28), wherein in step a), the gripping of the container is conducted in such a manner that the gripping tool is not present over a vertical line of an opening of the container.

(30) The liquid transport method as described in any one of (25) to (29), wherein the liquid is a culture medium.

In accordance with an aspect, a liquid transport method in processing of cells is disclosed, the liquid transport method comprising: a) a step in which lateral sides of a container holding a liquid is gripped by a gripping tool of a robot from a cassette configured to hold a plurality of containers, the cassette having a plurality of recessed parts each shaped corresponding to a bottom surface of the container, the gripping of the container being conducted in such a manner that the gripping tool is not present over a vertical line of an opening of the container; b) a step in which the liquid in the container is transported into a collection container by rotating the gripped container and orienting the opening of the gripped container toward a vertically lower direction; and wherein in steps a) and b), the robot operates in such a manner as not to pass over a vertical line of an opening of the collection container.

In accordance with another aspect, a cell processing system is disclosed, which is a system for use in processing of cells by use of a container, the cell processing system comprising: a base provided with a plurality of processing areas for performing processing by use of the container and a carrying-in/carrying-out area where things for use in the processing can be carried in and carried out; a robot that is provided on the base and has a gripping tool capable of gripping at least part of the container, the robot being adjacent to each of the plurality of processing areas; a housing that covers the processing areas, the robot, and at least part of the carrying-in/carrying-out area and is able to maintain cleanliness of an inside of the housing; at least one working section that is disposed on the housing or the base and is configured in such a manner that manual operation in the housing from outside of the housing can be performed thereby; wherein the gripping tool of the robot can reach each of the processing areas; the housing is configured such that a part of the housing adjacent to the carrying-in/carrying-out area can be opened and closed; the working section is configured such that its workable area overlaps with the processing area and/or the carrying-in/carrying-out area, and things for use in the processing can be moved between the respective processing areas and the carrying-in/carrying-out area through the working section; at least one openable and closeable slide shutter, the at least one openable and closeable shutter configured to produce a closed system when the at least one shutter is closed; and a plurality of suction portions in the base and in a vicinity of the at least one shutter, the plurality of suction portions configured to generate a clean space having a reduced-pressure state in the clean space.

According to the present disclosure, a cell processing system is disclosed, which enables efficient production of cell cultures and which has a comparatively simple configuration, and a cell processing method, a liquid transport method, and a gripping tool which are for efficient production of cell cultures.

BRIEF DESCRIPTION OF THE DRAWINGS

FIGS. 6(a)-6(c) show schematic views for illustrating an operation of the gripping tool shown in FIG. 4.

FIGS. 12(a)-12(g) show schematic views for illustrating a liquid transport method according to the first embodiment of the present disclosure.

FIGS. 13(a)-13(e) show schematic views for illustrating a conventional liquid transport method.

DETAILED DESCRIPTION

Figure 1:
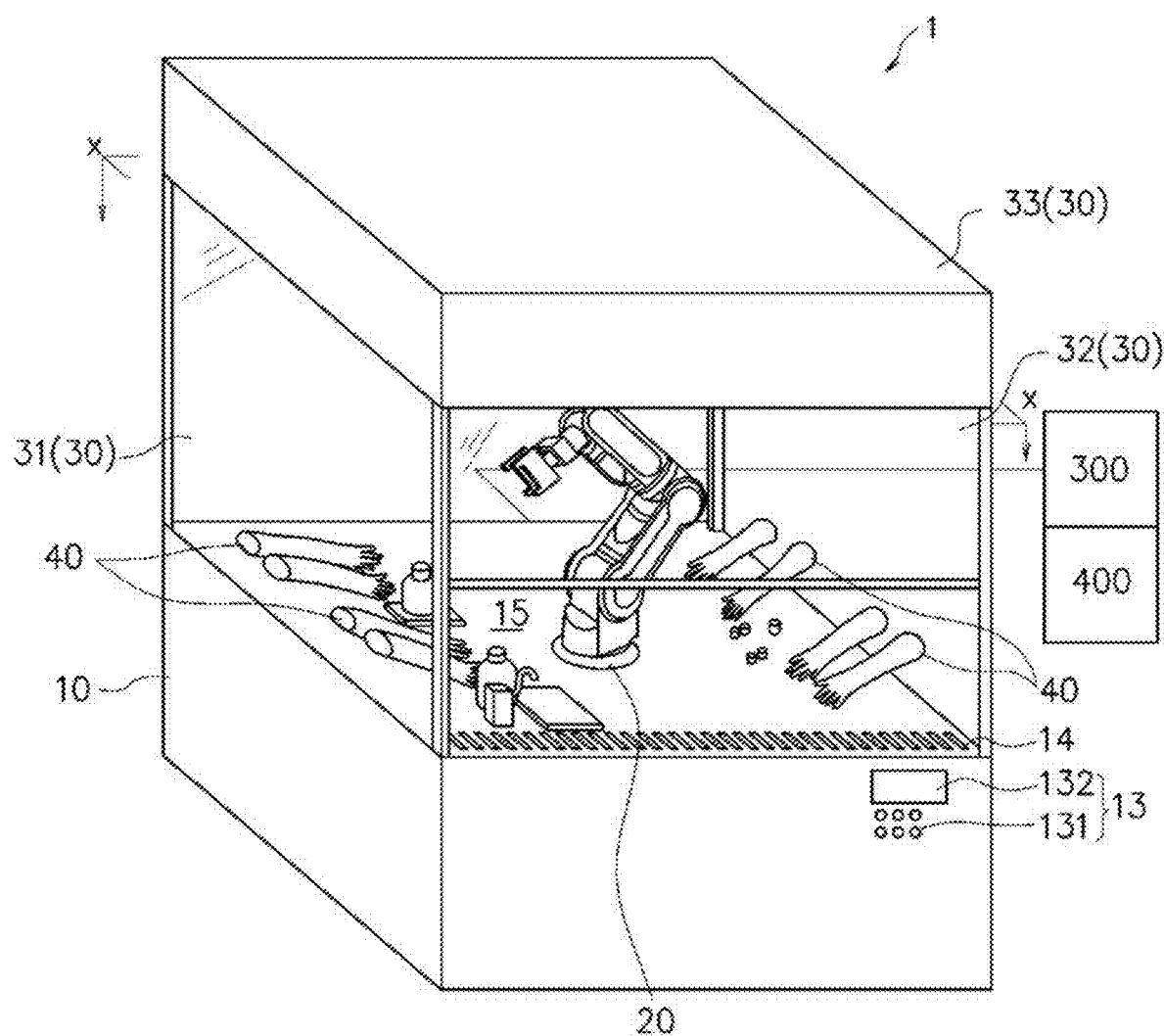
FIG. 1 is a schematic diagram of a cell processing system according to a first embodiment of the present disclosure.

Preferred embodiments of the present disclosure will be described in detail below, referring to the drawings.

Note that in each of the figures in the present application, the sizes of respective members are appropriately exaggerated, for easy explanation, and the respective members shown in the figures are not shown in the actual sizes.

First, a first embodiment of the present disclosure will be described.

A cell processing system 1 illustrated in FIG. 1 is used for processing (treatment) of cells using a container 100, and used particularly for discharging a liquid L from the container 100 and pouring (dispensing) the liquid L into the container 100, in culturing cells by use of the container 100 to obtain a cell culture. In the present embodiment, the liquid L is a culture medium, and the cell processing system 1 is a culture medium exchange system used for exchange of the culture medium (liquid L) in the container 100.

In addition, cells to be used in the processing in the cell processing system 1 are not particularly limited, and examples of the cells include cells harvested from a subject, and cryopreserved cells.

More specifically, the cells which can be used in the cell processing system 1 are not particularly limited, and examples of the cells include adherent cells (adhesive cells). Examples of the adherent cells include adherent somatic cells (for example, myocardial cells, fibroblasts, epithelial cells, endothelial cells, hepatic cells, pancreatic cells, renal cells, adrenal cells, periodontal ligament cells, gingival cells, periosteal cells, skin cells, synovial cells, cartilage cells, etc.) and stem cells (for example, myoblasts, cardiac stem cells and the like tissue stem cells, embryonic stem cells, induced pluripotent stem (iPS) cells and the like pluripotent stem cells, mesenchymal stem cells, etc.). The somatic cells may be those differentiated from stem cells, particularly iPS cells. Examples of such cells include myoblasts (for example, skeletal myoblasts), mesenchymal stem cells (for example, those derived from bone marrow, adipose tissue, peripheral blood, skin, hair root, muscular tissue, uterine mucosa, placenta, or umbilical cord blood), myocardial cells, fibroblasts, cardiac stem cells, embryonic stem cells, iPS cells, synovial cells, cartilage cells, epithelial cells (for example, mouse mucosa epithelial cells, retinal pigment epithelial cells, nasal epithelial cells, etc.), endothelial cells (for example, vascular endothelial cells), hepatic cells (for example, hepatic parenchymal cells), pancreatic cells (for example, islet cells), renal cells, adrenal cells, periodontal ligament cells, gingival cells, periosteal cells, skin cells, etc.

In addition, by cell culture including the processing conducted utilizing the cell processing system 1, a cell culture wherein cells are interlocked each other such as, for example, a sheet-shaped cell culture can be obtained.

Herein the "sheet-shaped cell culture" refers to a sheet-shaped body wherein cells are interlocked each other. The cells in the sheet-shaped cell culture may be interlocked each other directly (inclusive of the case of interconnection through cell elements such as adhesion molecules) and/or through an intervening substance. In accordance with an exemplary embodiment, the intervening substance is not particularly limited so long as it is a substance capable of at least physically (mechanically) interlock the cells, and examples thereof include an extracellular matrix. The intervening substance is preferably one derived from cells, for example, particularly one that is derived from the cells constituting the sheet-shaped cell culture. The cells are interlocked at least physically (mechanically), and may be further interlocked functionally, for example, chemically or electrically. The sheet-shaped cell culture may be one that is composed of one cell layer (monolayer), or may be one that is composed of two or more cell layers (laminated (multi-layer), for example, two layers, three layers, four layers, five layers, or six layers).

In accordance with an exemplary embodiment, the sheet-shaped cell culture preferably does not include a scaffold (support). A scaffold may be used in the technical field by adhering cells onto its surface and/or to its inside for the purpose of maintaining the physical integrity of the sheet-shaped cell culture, and known examples of the scaffold include a membrane made of polyvinylidene difluoride (PVDF). In addition, preferably, the sheet-shaped cell culture is composed of a substance or substances derived from the cells constituting the sheet-shaped cell culture and does not include other substances.

In accordance with an exemplary embodiment, the aforementioned cells can be derived from any organism that can be treated by the sheet-shaped cell culture. Such an organism is not limited examples, and examples of the organisms can include humans, nonhuman primates, dogs, cats, pigs, horses, goats, sheep, rodent animals (for example, mice, rats, hamsters, guinea pigs), and rabbits.

The cells to be used for forming the sheet-shaped cell culture may be one kind of cells, or may be two kinds of cells. In the case where the cells for forming the sheet-shaped cell culture are two or more kinds of cells, the proportion (purity) of the most abundant kind of cells is, for example, not less than approximately 60%, preferably not less than approximately 70%, and more preferably not less than approximately 75%, at the start of culture for forming a sheet-shaped body or at the end of production of the sheet-shaped cell culture.

Figure 7:
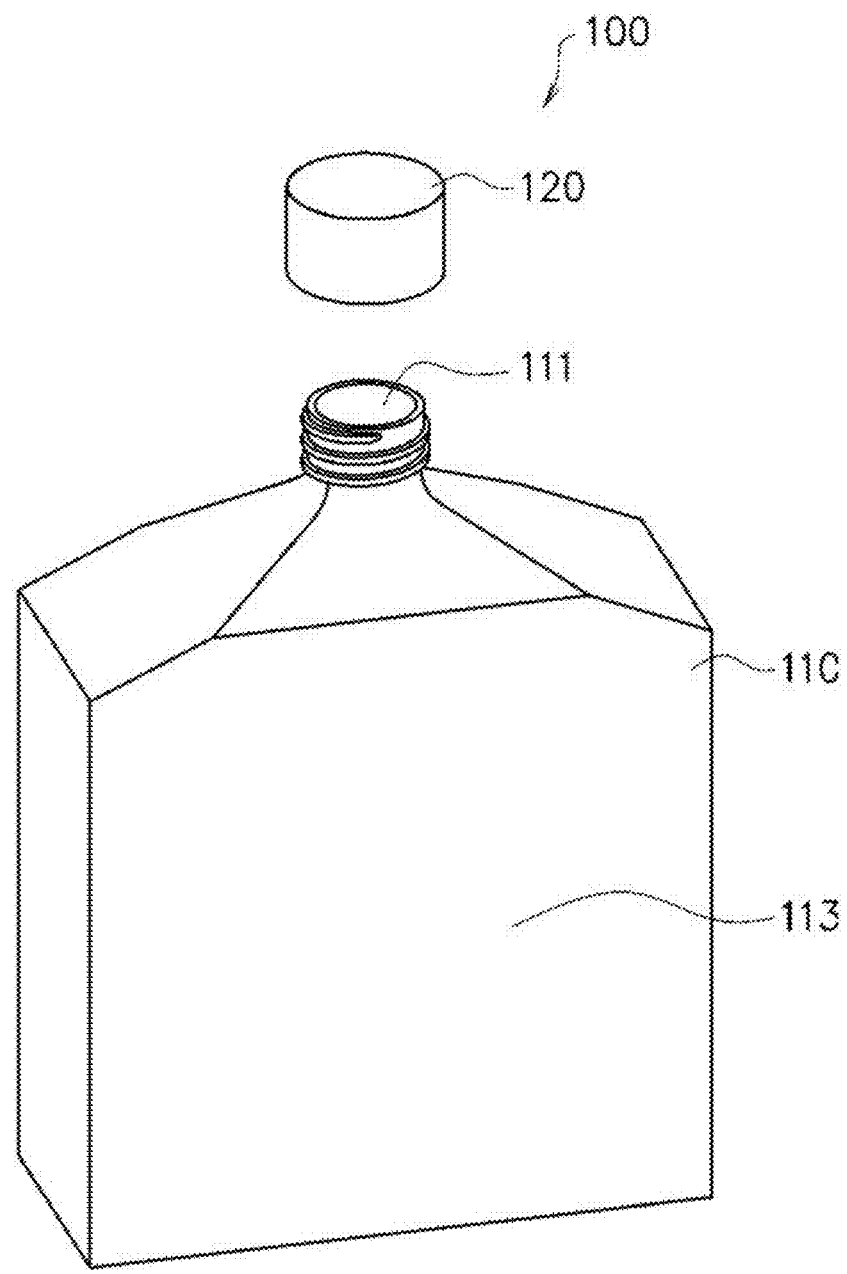
FIG. 7 is a schematic view showing an example of a container for use in the cell processing system according to the first embodiment.
Figure 8:
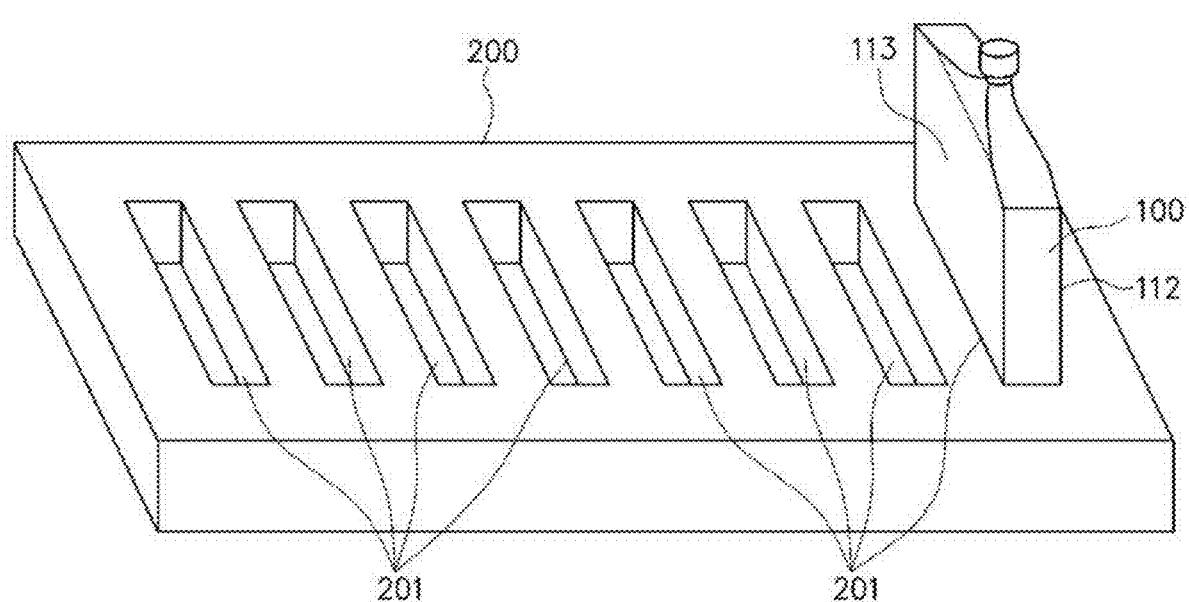
FIG. 8 is a schematic view showing an example of a cassette for the containers for use in the cell processing system according to the first embodiment.
Figure 9:
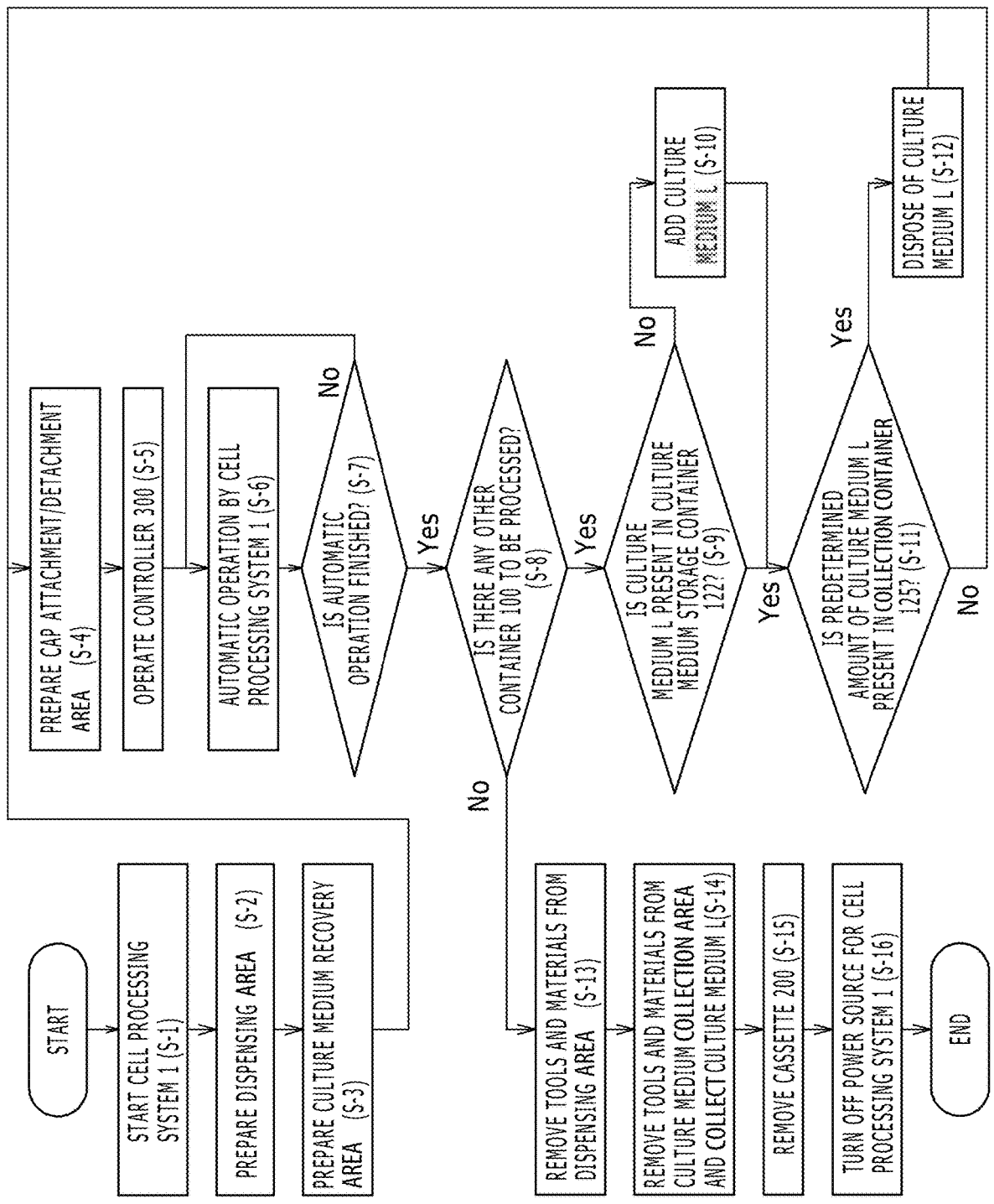
FIG. 9 is a flow chart for explaining a cell processing method according to the first embodiment of the present disclosure.

In addition, in the present embodiment, as shown in FIGS. 7 and 8, the container 100 is a cell culture flask, and includes a container main body 110 having an opening 111, and a cap 120 configured to be capable of screw engagement with the opening 111 of the container main body 110 and capable of thereby closing the opening 111. The container main body 110 has two main surfaces 112 and 113 as side surfaces thereof, and can be used for culture of cells with either of the main surfaces 112 and 113 as a lower surface.

Note that in the present embodiment the cell processing system 1 is for operating a plurality of containers 100, and in management and operation of the plurality of containers 100, a cassette 200 as depicted in FIG. 8 can be used. The cassette 200 can be a plate-shaped base provided with a plurality of recessed parts 201 on a main surface thereof. Each of the recessed parts 201 is shaped correspondingly to the shape of the container main body 110 such that the container 100 can be disposed in the recessed part 201 with the cap 120 oriented upward. In addition, the recessed parts 201 can be provided in a row such that the plurality of containers 100 can be aligned in such a manner that the main surfaces 112 of the containers 100 are parallel to one another. In addition, the cassette 200 is provided, in a main surface on the side opposite to the main surface formed with the recessed parts 201, with securing holes (not shown) in which securing pins 127 to be described later can be engaged.

Figure 2:
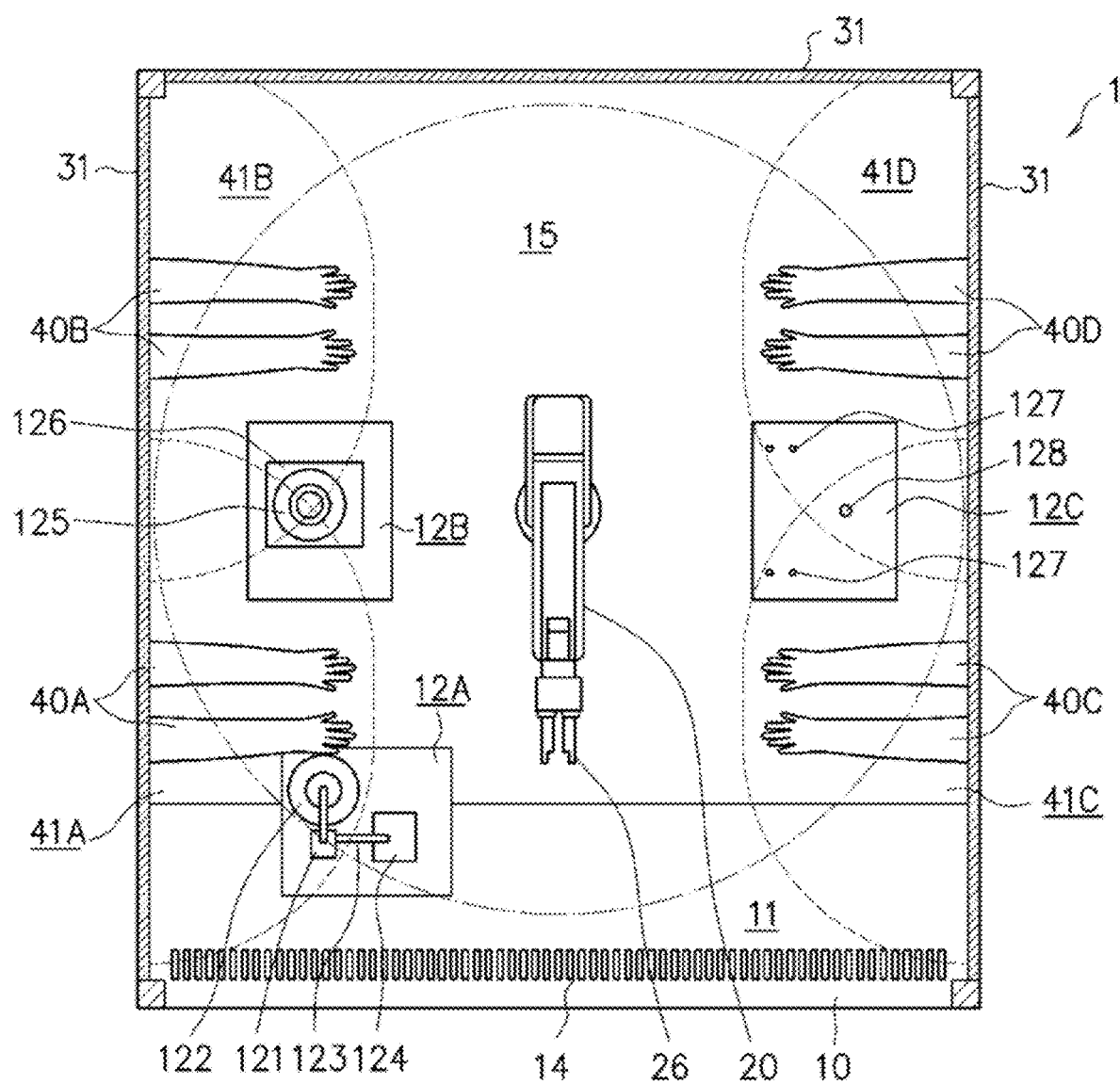
FIG. 2 is a plan sectional view of the cell processing system shown along lines X-X in FIG. 1.

The cell processing system 1 illustrated in FIGS. 1 and 2 includes a base 10, a robot 20, a housing 30, and working sections 40.

The base 10 is a working table on which to perform processing of cells in the cell processing system 1. As shown in FIG. 2, the base 10 is rectangular in plan-view shape. On the base 10, a carrying-in/carrying-out area 11 is disposed in the vicinity of one end, and a plurality of processing areas 12A to 12C are disposed in other areas than the carrying-in/carrying-out area 11. In addition, the base 10 is provided with an operation section 13 at a side surface in the vicinity of the carrying-in/carrying-out area 11.

The carrying-in/carrying-out area 11 is an area used for carrying-in and carrying-out of the containers 100, the cassette 200, materials necessary for processing of cells, and things for use in processing such as chemicals, culture medium, instruments, and devices. In the present embodiment, the carrying-in/carrying-out area 11 is entirely disposed under a space (clean space) 15 formed by the housing 30 which is described later. In accordance with an exemplary embodiment, an operator present in the external environment can dispose things to be used in the processing on the carrying-in/carrying-out area 11 through a shutter 32 of the housing 30 which will be described later. In addition, if necessary, the operator can perform appropriate operations over the carrying-in/carrying-out area 11.

In accordance with an exemplary embodiment, the processing areas 12A to 12C are disposed adjacently to the robot 20 and the working sections 40 which will be described later. The processing areas 12A to 12C are areas in which processing is performed. In the processing areas 12A and 12C, things for use in the processing is disposed in accordance with the contents of the processing.

Specifically, the processing area 12A is a dispensing area in which to dispense a liquid into the container 100. Therefore, a dispensing pump 121, a culture medium storage container 122 for storing a culture medium, a tube 123 for supplying the culture medium from the culture medium storage container 122 into the container 100 by the dispensing pump 121, and a liquid measurement sensor 124 for measuring the amount of the liquid dispensed into the container 100 are disposed in the processing area 12A.

The processing area 12B is a culture medium collection area for disposing of and collecting the culture medium in the container 100. A collection container 125 for collecting the culture medium transported from the container 100 and a sensor 126 for measuring the collection amount are disposed in the processing area 12B. In accordance with an exemplary embodiment, the collection container 125 is a bottle having a comparatively large capacity, and the sensor 126 is a weight sensor disposed under the collection container 125. Note that the sensor is not limited to this one, and may be, for example, an optical sensor that optically detects the amount of liquid.

In accordance with an exemplary embodiment, the processing area 12C is a cap attachment/detachment area for attaching and detaching the cap 120 of the container 100.

Securing pins 127 as securing means for securing the cassette 200 for the containers 100 and a cap depository 128 for supporting the cap 120 detached from the container 100 are disposed in the processing area 12C. The securing pins 127 have shapes corresponding to the securing holes in the cassette 200, and can secure the cassette 200 through engagement with the securing holes. The cap depository 128 is shaped correspondingly to the cap 120, and is configured to be capable of screw engagement with the cap 120.

The operation section 13 shown in FIG. 1 is configured such as to perform at least part of operations for controlling the robot 20 in the cell processing system 1, respective instruments in the processing areas 12A to 12C, and the atmosphere (environment) in the space 15 which will be described later, and includes various input sections 131 and a display section 132.

The input sections 131 are configured in such a manner that commands to the cell processing system 1 can be inputted by the operator. The commands inputted at the input sections 131 are transmitted to a control section (not shown) in the base 10, and control of the cell processing system 1, specifically, control of the robot 20 and the atmosphere is performed by the control section. Note that while the input sections 131 are composed of pluralities of buttons and handles in the present embodiment, these are not restrictive. For example, in accordance with an exemplary embodiment, the input sections 131 can be configured by use of pointing devices such as a mouse, a trackball, and a pen tablet, connection terminals such as a keyboard, a touch panel, or input, output, or input/output terminals, a joystick, or a three-dimensional tactile-sense/force-sense interface device, either singly or in combination.

The display section 132 is a display for displaying information concerning the cell processing system 1, such as the state of the cell processing system 1 and the contents of inputted commands. The display section 132 is configured to be capable of communication with the control section, and can display information in response to the commands from the control section. Note that while the display section 132 is a display in the present embodiment, this is not restrictive. For example, the display section 132 may be lamps, a touch panel or the like, or may be configured by a combination of these.

In addition, the base 10 is provided with suction ports 14 in the vicinity of the shutter 32 to be described later, in the carrying-in/carrying-out area 11. Air in the clean space 15 is sucked through the suction ports 14 to establish a reduced-pressure state in the clean space 15, whereby unintentional leakage to the exterior of the cell processing system 1 can be prevented from occurring. In addition, an airflow generated between the suction ports 14 and an air supply port which will be described later form an air curtain in the vicinity of the shutter 32, whereby foreign matter can be prevented from mixing into the clean space 15 from the exterior of the cell processing system 1. In accordance with an exemplary embodiment, the air sucked through the suction ports 14 is appropriately sterilized by sterilizing means (not shown) such as a high efficiency particular air (HEPA) filter disposed in the cell processing system 1, and discharged to the exterior of the cell processing system 1.

Figure 3:
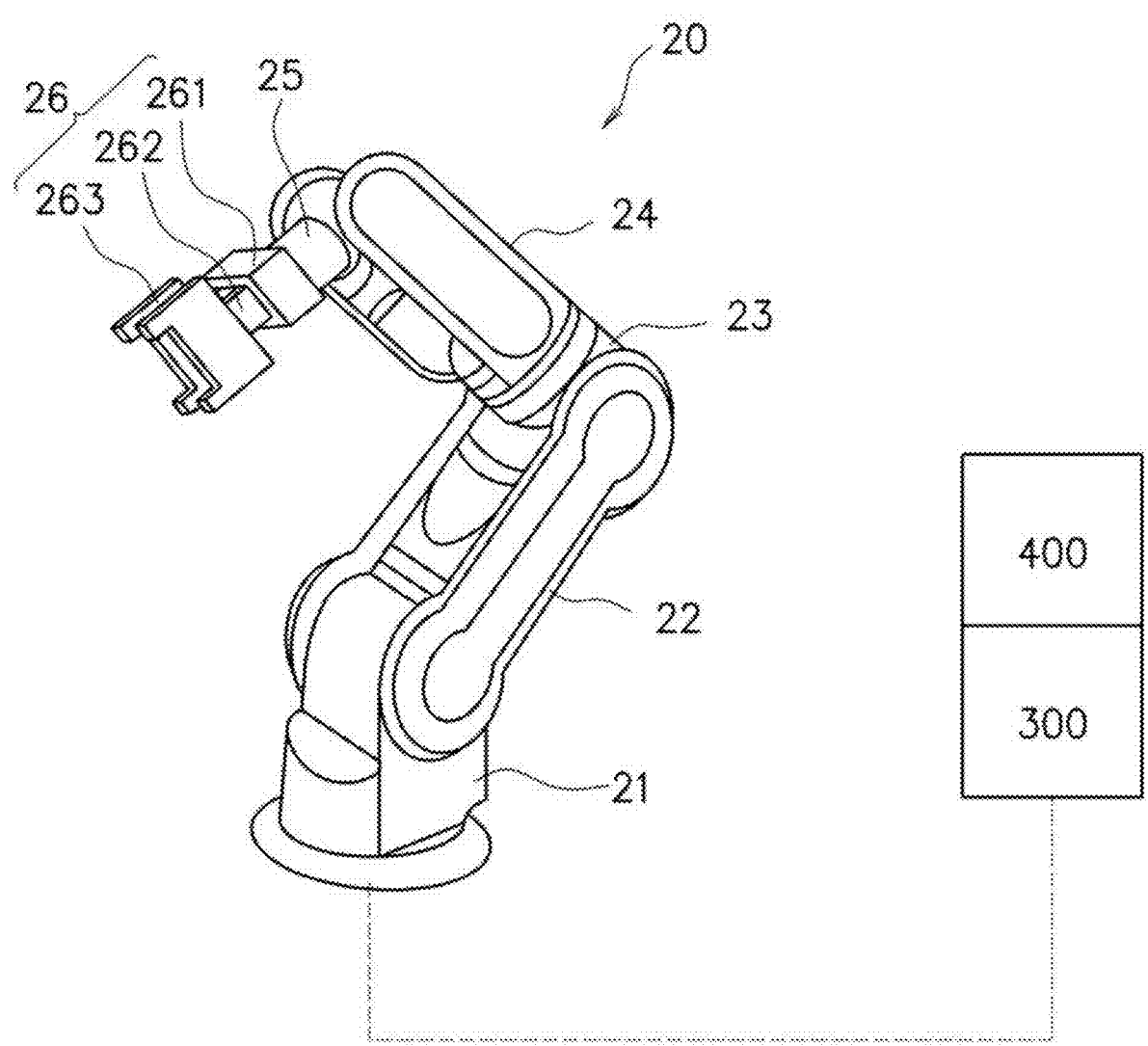
FIG. 3 is a perspective view of a robot provided in the cell processing system shown in FIG. 1.

As illustrated in FIG. 3, the robot 20 is a vertical articulated robot disposed in the vicinity of the center of the base 10. In accordance with an exemplary embodiment, the robot 20 has six axes. The robot 20 can include a base 21 which can be turned relative to the base 10, a first arm 22 which is interlocked to the base 21 and can be tilted relative to a vertical axis about which the base 21 is turned, a second arm proximal section 23 which is interlocked to a distal side of the first arm 22 and can be tilted relative to the first arm 22, a second arm distal section 24 which is interlocked to a distal side of the second arm proximal section 23 and can be rotated relative to an axial direction of the second arm proximal section 23, a hand section 25 which is interlocked to a distal side of the second arm distal section 24 and can be tilted relative to an axial direction of the second arm distal section 24, and a gripping tool (gripper) 26 interlocked to the hand section 25. In accordance with an exemplary embodiment, the hand section 25 is configured to be rotatable about an axial direction thereof.

In addition, the robot 20 is configured such that its gripping tool 26 can reach an area indicated by an alternate long and short dash line in FIG. 2 and, therefore, can reach a desired position in each of the processing areas 12A to 12C in a desired posture. As a result, operations in the processing areas 12A to 12C by the robot 20 can be performed.

In addition, the robot 20 is connected to a controller 300 and a control terminal 400 disposed in the exterior of the cell processing system 1 shown in FIG. 1, and can automatically perform operations according to the commands inputted from the control terminal 400.

Configured in this manner, the robot 20 can perform determination of the position and posture of the gripping tool 26 as well as rotation and opening/closing operations of the gripping tool 26, whereby the container 100 can be gripped and operated by the gripping tool 26. More specifically, for example, by gripping the container 100 by the gripping tool 26, the container 100 can be transported, tilted, and rotated, and, by gripping the cap 120 and rotating the gripping tool 26, the cap 120 can be detached from the container main body 110 or attached to the container main body 110.

Now, the gripping tool 26 will be described more in detail.

Figure 4:
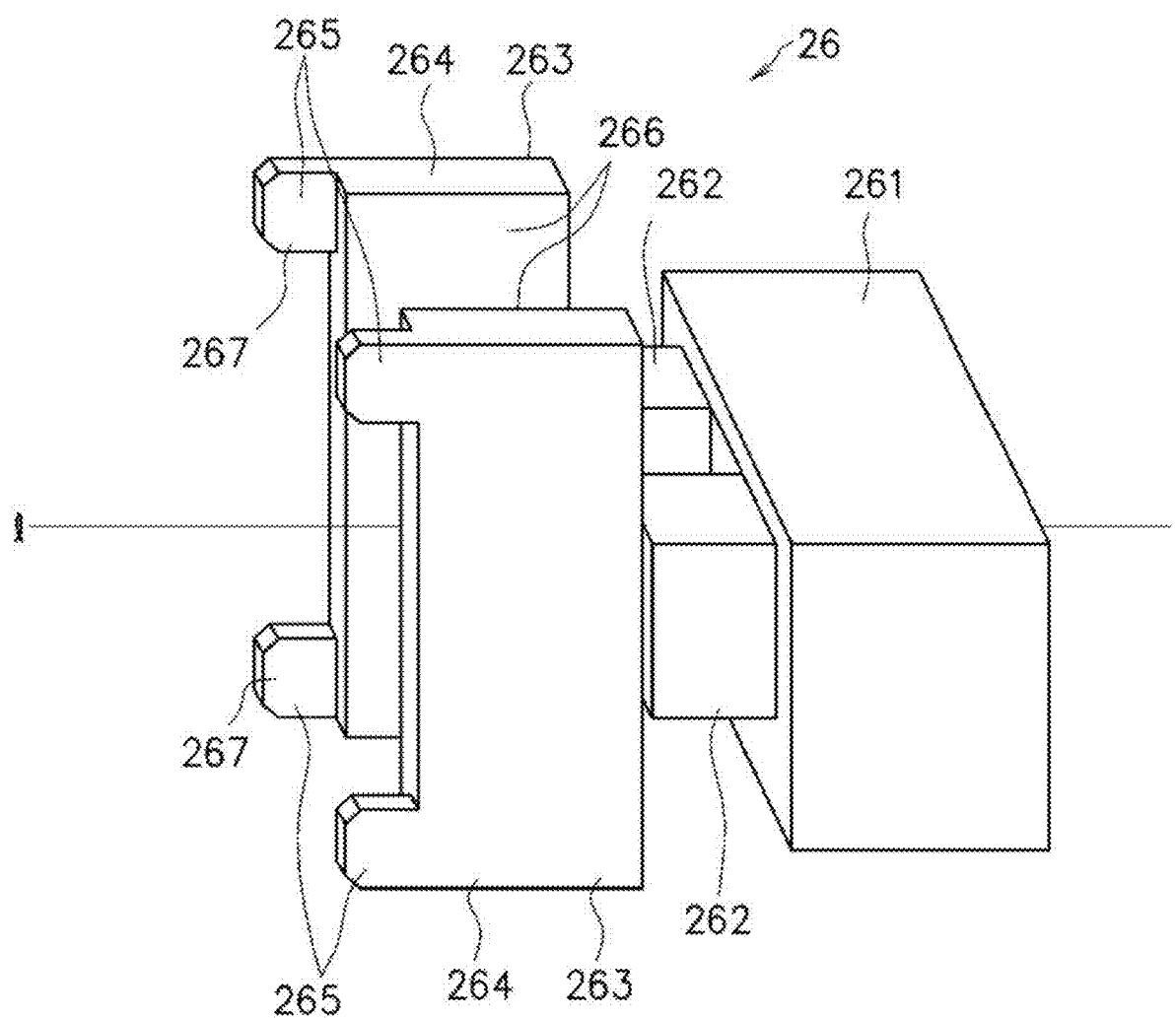
FIG. 4 is a partial enlarged view of a gripping tool of the robot provided in the cell processing system shown in FIG. 1.

The gripping tool 26 depicted in FIG. 4 is a parallel gripper, and can include a gripping tool main body 261 interlocked to the hand section 25 on the proximal side thereof, a pair of guide members 262 disposed on the distal side of the gripping tool main body 261 and slidable, and a pair of claw sections (fingers) 263 secured to the guide members 262.

The gripping tool main body 261 is provided therein with an actuator and a linear guide (both not shown), and operates the guide members 262 by being externally supplied with a command and power such as electric power. The guide members 262 are secured in the direction of sliding by the linear guide, and the guide members 262 can be accurately brought closer to or away from each other.

In accordance with an exemplary embodiment, the pair of claw sections 263 are secured individually to the pair of guide members 262, and can be brought closer to or away from each other according to the operation of the guide members 262. As a result, the claw sections 263 can grip at least part of the container 100.

Figure 5A:
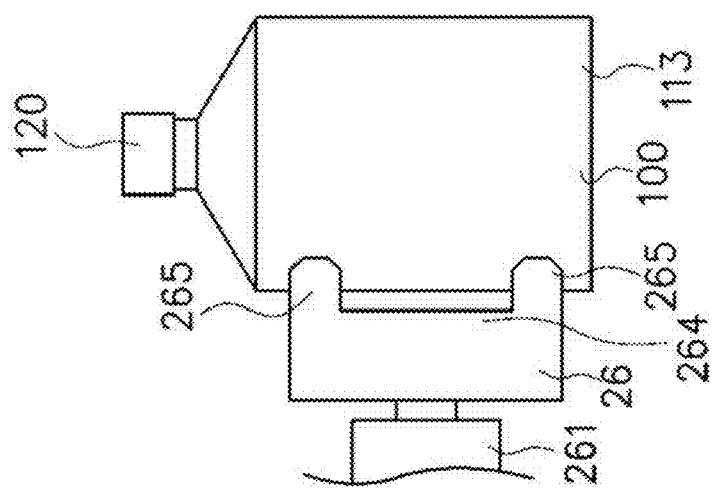
FIGS. 5(a)-5(c) show schematic views for illustrating an operation of the gripping tool shown in FIG. 4.
Figure 5B:
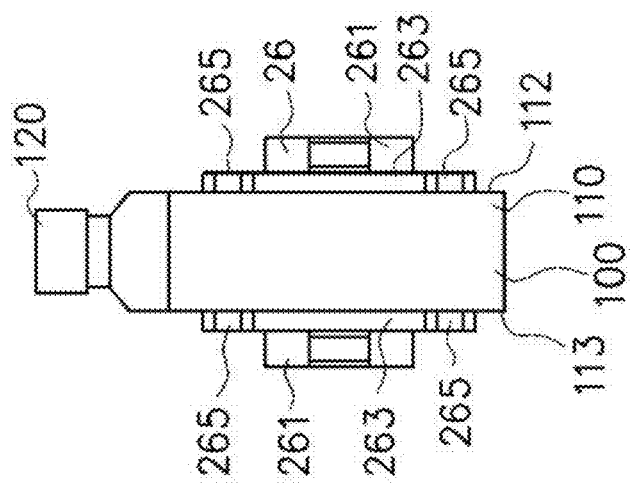
Figure 5C:
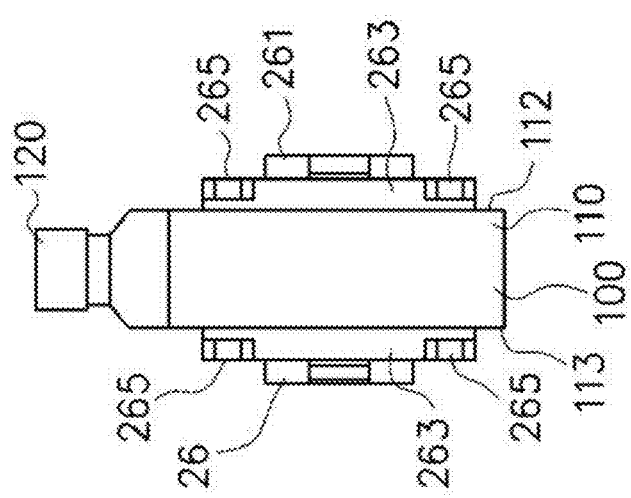

The claw section 263 includes a first gripping section 264 provided on a proximal side, and a second gripping section 265 provided on the distal side (distal tip side) with reference to the first gripping section 264. In addition, the second gripping section 265 is configured such that the separated distance between its gripping surfaces 267 is greater than the separated distance between gripping surfaces 266 of the first gripping section 264. Since the claw sections 263 have two sets of gripping sections differing in separated distance, namely, in gripping width, the size of the gripping tool 26 can be reduced by reducing a stroke of the gripping tool 26, and bodies (works) with different sizes can be gripped. As a result, as shown in FIGS. 6(a) to 6(c), the cap 120 of the container 100 can be gripped by the first gripping section 264, and, on the other hand, as shown in FIGS. 5(a) to 5(c), the container main body 110 of the container 100 can be gripped by the second gripping section 265. In addition, by rotating the first gripping section 264 together with the claw sections 263 while gripping the cap 120, the cap 120 can be detached from the container main body 110 and to attach the cap 120 to the container main body 110.

In addition, anti-slipping portions are disposed on the gripping surfaces 266 of the first gripping section 264. This helps ensure that the cap 120 can be held by the first gripping section 264 more securely, and, in the case of rotating the cap 120 by the first gripping section 264, a rotating force can be transmitted from the first gripping section 264 to the cap 120 more reliably. In addition, as a result, for example, the gripping force by the first gripping section 264 can be set comparatively weak, whereby the work as an object to be gripped, such as the cap 120, is prevented from being damaged. The method for configuring the anti-slipping portions is not particularly limited, and examples of the method include a method wherein a high-frictional-coefficient material such as rubber or elastomer is disposed on the gripping surfaces, and a method wherein the gripping surfaces 266 are knurled and thereby enhanced in friction.

In addition, as shown in FIG. 4, the second gripping section 265 has a configuration wherein part thereof is omitted in the vicinity of a center axis I of the first gripping section 264. This ensures that when the cap 120 is gripped by the first gripping section 264 and the cap 120 together with the first gripping section 264 is rotated with the center axis I as an axis of rotation, the second gripping section 265 can be prevented from interfering with the container main body 110 of the container 100.

Note that herein the center axis I is a center axis as viewed from the pair of gripping surfaces 266, specifically a center axis which is parallel to the main surfaces of the pair of gripping surfaces 266 of the first gripping sections 264 and is directed from the proximal side toward the distal side of the first gripping section 264.

More specifically, in the present embodiment, the second gripping section 265 is disposed at a position corresponding to both end portions on lateral sides of the gripping surfaces 266 of the first gripping section 264. Specifically, for example, the second gripping section 265 is composed of four claws projecting toward the distal side from both end portions on lateral sides of the first gripping section 264, and is configured such as to grip two points individually by two claws. By such a configuration, as shown in FIG. 6(c), the second gripping section 265 can be more securely prevented from interfering with the container main body 110. In addition, as depicted in FIG. 5(c), the second gripping section 265 can grip and fix the container main body 110 at a plurality of positions, which helps ensure that when the container main body 110 is gripped by the second gripping section 265, the container main body 110 is prevented from being rotated and tilted unintentionally. In addition, since the position of the second gripping section 265 is at both ends, in the presence of a rotation moment generated about one side (for example, the lower side) of the second gripping section 265, the other side of the second gripping section 265 can sufficiently support the container main body 110.

In accordance with an exemplary embodiment, anti-slipping portions are disposed on the gripping surfaces 267 of the second gripping section 265. As a result, the container 100 can be gripped relatively more securely by the second gripping section 265. In addition, a work such as the container 100 can be sufficiently gripped even with a comparatively weak gripping force, so that the work such as the container 100 can be prevented from being broken.

The housing 30 shown in FIGS. 1 and 2 is configured such as to cover the carrying-in/carrying-out area 11, the processing areas 12A and 12C, and the robot 20 on the base 10 and to shield the space 15 over the base 10 from the atmosphere in the outside of the cell processing system 1. The housing 30 includes side walls 31 and the shutter 32 erected in the vicinity of peripheral portions of the base 10, and a ceiling section 33 which seals from above the space 15 defined by the side walls 31 and the shutter 21.

In accordance with an exemplary embodiment, a fan-filter unit (not shown) composed by combining a filter such as a HEPA filter with a fan can be incorporated in the ceiling section 33. Air is sucked from the exterior of the cell processing system 1, and is sterilized and deprived of foreign matter, and clean air is supplied through an air supply port (not shown) onto the space 15. With clean air thus supplied to the upper side of the base 10 while shielding from the atmosphere in the outside of the cell processing system 1, the space 15 over the base 10 becomes a clean space 15 where a clean atmosphere is maintained.

In accordance with an exemplary embodiment, the cell processing system 1 is configured in such a manner that the cleanliness in the clean space 15, for example, is International Organization for Standardization (ISO) class 1 to 9, preferably ISO class 1 to 8, more preferably ISO class 1 to 7, in accordance with ISO 14644-1.

In addition, the shutter 32 is a part provided adjacently to the carrying-in/carrying-out area 11, and is a slide shutter configured to be openable and closable. When the shutter 32 is closed, the clean space 15 is a closed system, and the clean atmosphere therein is maintained more securely. On the other hand, when the shutter 32 is opened, things for use in processing can be moved between the cell processing system 1 and the external environment through the carrying-in/carrying-out area 11, and, in addition, the operator present in the external environment can perform operations in the carrying-in/carrying-out area 11. In addition, in accordance with an exemplary embodiment, the size of the opening defined by the shutter 32 can be appropriately controlled.

In accordance with an exemplary embodiment, the side walls 31 and the shutter 32 constituting the housing 30 are both formed of a transparent material, for example, resin, so that the inside of the housing 30 can be observed therethrough.

The working sections 40A to 40D are instruments or tools which are disposed along the side walls 31 of the housing 30 and configured such that manual operations (workings) within the housing 30, namely, for example, in the clean space 15 from the exterior of the housing 30 can be performed. In the present embodiment, the working sections 40A to 40D are pairs of gloves disposed such as to penetrate the side wall 31, which helps permit the operator present in the exterior of the cell processing system 1 to perform transport of things necessary for processing of cells using the container 100 and preparation for the processing, in the clean space 15 by use of the working sections 40A to 40D.

In addition, the areas in which the working sections 40A to 40D can be operated, namely, working areas 41A to 41D, indicated by broken lines in FIG. 2 are overlapping with some of the processing areas 12A to 12C and/or the carrying-in/carrying-out area 11. Specifically, the working section 40A has its working area 41A overlapping with the carrying-in/carrying-out area 11 and the processing areas 12A and 12B. The working section 40B has its working area 41B overlapping with the processing area 12B. The working section 40C has its working area 41C overlapping with the carrying-in/carrying-out area 11 and the processing area 12C. The working section 40D has its working area 41D overlapping with the processing area 12C.

Further, although the working areas 41B and 41D of the working sections 40B and 40D do not overlap with the carrying-in/carrying-out area 11, they on the other hand overlap with the working areas 41A and 41C of the working sections 40A and 40C to which they are adjacent, respectively, which helps ensure that although the working sections 40B and 40D have their working areas 41B and 41D not overlapping with the carrying-in/carrying-out area 11, they are configured such that the things for use in the processing can be moved through the working areas 41A and 41C of the working sections 40A and 40C with which they overlap.

According to the working sections 40A to 40D configured as above, manual preparation for processing, namely, carrying-in and carrying-out of things for use in the processing, disposition of the things, can be performed in each of the processing areas 12A to 12C. The preparation for each processing is generally complicated, but, by manually performing such operations, the device configuration of the cell processing system 1 can be made to be comparatively simple. In addition, for example, confirmation of the amount of a culture medium necessary for exchange, confirmation of disposed states of respective instruments for use in processing, etc. are more readily carried out by manual operation by the operator than by introduction of devices provided with sensors or the like. On the other hand, in regard of comparatively simple processing which need to be carried out repeatedly, such as attachment and detachment of the cap 120, or disposal and dispensing of the liquid (culture medium), the operations can be carried out relatively speedily and accurately by the robot 20.

In the cell processing system 1, comparatively simple operations which need to be performed repeatedly are automatically carried out by the cell processing system 1 including the robot 20, and the other operations are carried out by the operator. Where the operations to be performed are thus divided among the operator and the robot 20 in accordance with the kinds of the operations, the operations inclusive of the processing conducted in the cell processing system 1 can be carried out relatively more efficiently, and the device configuration of the cell processing system 1 can be made to be comparatively simple.

In accordance with an exemplary embodiment, the gripping tool 26 can include the first gripping section 264 and the second gripping section 265 which are different in separated distance as above-mentioned, and part of the second gripping section 265 is omitted in the vicinity of the center axis I of the first gripping section 264. According to this configuration, differently sized works such as the container main body 110 and the cap 120 can be gripped by the same gripping tool 26. In addition, even in the case where the cap 120 is rotated by the first gripping section 264, interference between the second gripping section 265 and the container main body 110 can be prevented from occurring. As a result, a situation wherein a plurality of robots are disposed for differently sized works or wherein the gripping tool is enlarged in mechanism for enlarging the stroke of the gripping tool, with the result of enlargement of the overall size of the robot, can be obviated. Accordingly, by adopting such a configuration as that of the gripping tool 26, the configuration of the cell processing system 1 can be relatively simplified.

Now, a cell processing method and a liquid transport method of the present embodiment using the aforementioned cell processing system 1 will be described below.

In accordance with an exemplary embodiment, since the cell processing system 1 is one for use in exchange of a culture medium, the liquid to be exchanged is a culture medium in the present embodiment. In addition, description will be made based on a situation in which in the container 100 to be used, a sheet-shaped cell culture (cell tissue) 114 cultured by a culture medium L is supported on (adhered to) an inner wall surface of a main surface 113.

In addition, the cell processing method of the present embodiment includes, in regard of processing of cells:

1) a step of disposing n (where n is an integer of not less than 2) containers which are to be processed in a predetermined order;

2) a step of detaching a cap of a container to be processed i-thly (where i is an integer satisfying $2 \leq i \leq n$) from a container main body and attaching the cap to a container main body of a container processed (i−1)thly, by a robot; and 3) a step of performing processing by use of the container to be processed i-thly.

In addition, the liquid transport method of the present embodiment includes:

a) a step of gripping a container that holds a liquid by a gripping tool of a robot; and b) a step of transporting the liquid in the container to a collection container by rotating the gripped container, wherein in steps a) and b) the robot does not pass over a vertical line of an opening of the collection container.

First, a power source or sources for the cell processing system 1 and a peripheral system or systems for use therefor (for example, the controller 300 and the control terminal 400) are switched ON, to start the cell processing system 1 (S-1).

Next, instruments and materials for dispensing are disposed and prepared in the processing area 12A which is a dispensing area (S-2). More specifically, a substrate and materials are disposed on the carrying-in/carrying-out area 11, and thereafter the dispensing pump 121, the culture medium storage container 122, the tube 123, and the liquid measurement sensor 124 are disposed in the carrying-in/carrying-out area 11 by the operator either directly or by use of the working section 40A. In addition, after the disposition, priming is conducted, if necessary.

Subsequently, instruments and materials for collection of a culture medium are disposed and prepared in the processing area 12B which is a culture medium collection area (S-3). Specifically, the collection container 125 and the sensor 126 are disposed in the carrying-in/carrying-out area 11, and thereafter they are transported to the processing area 12B by the working section 40A. Thereafter, the collection container 125 and the sensor 126 are disposed by the working section 40A or the working section 40B.

Next, preparation for attachment/detachment of a cap is conducted in the processing area 12C which is a cap attachment/detachment area (S-4). Specifically, for example, a plurality of containers 100 each containing a culture medium is disposed on the cassette 200, and the cassette 200 is temporarily disposed in the carrying-in/carrying-out area 11. Thereafter, the cassette 200 is transported to the processing area 12C by the working section 40C. The cassette 200 is then secured to the processing area 12C by securing the securing pins 127 by the working section 40C or the working section 40D.

In accordance with an exemplary embodiment, the respective instruments or tools in the processing area 12A as the dispensing area and the processing area 12B as the culture medium collection area are also secured, if necessary, for example, by securing pins or the like within ranges having predetermined positioning accuracies.

In addition, in the present embodiment, the robot 20 is configured in such a manner that the order of priority of the containers 100 to be processed is determined according to the positions of the recessed parts 201 of the cassette 200. Therefore, the order in which to process the containers 100 is determined by disposing the containers 100 on the cassette 200. Then, the cassette 200 is secured to the processing area 12C, whereby step 1) according to the present embodiment can be carried out.

Subsequently, commands are inputted by the control terminal 400 to operate the controller 300 (S-5), and an automatic operation by the cell processing system 1 inclusive of the robot 20 is carried out (S-6). As a result, the cell processing system 1 including the robot 20 automatically performs predetermined operations according to the commands, and exchanges the culture medium in each of the containers 100.

Figure 10:
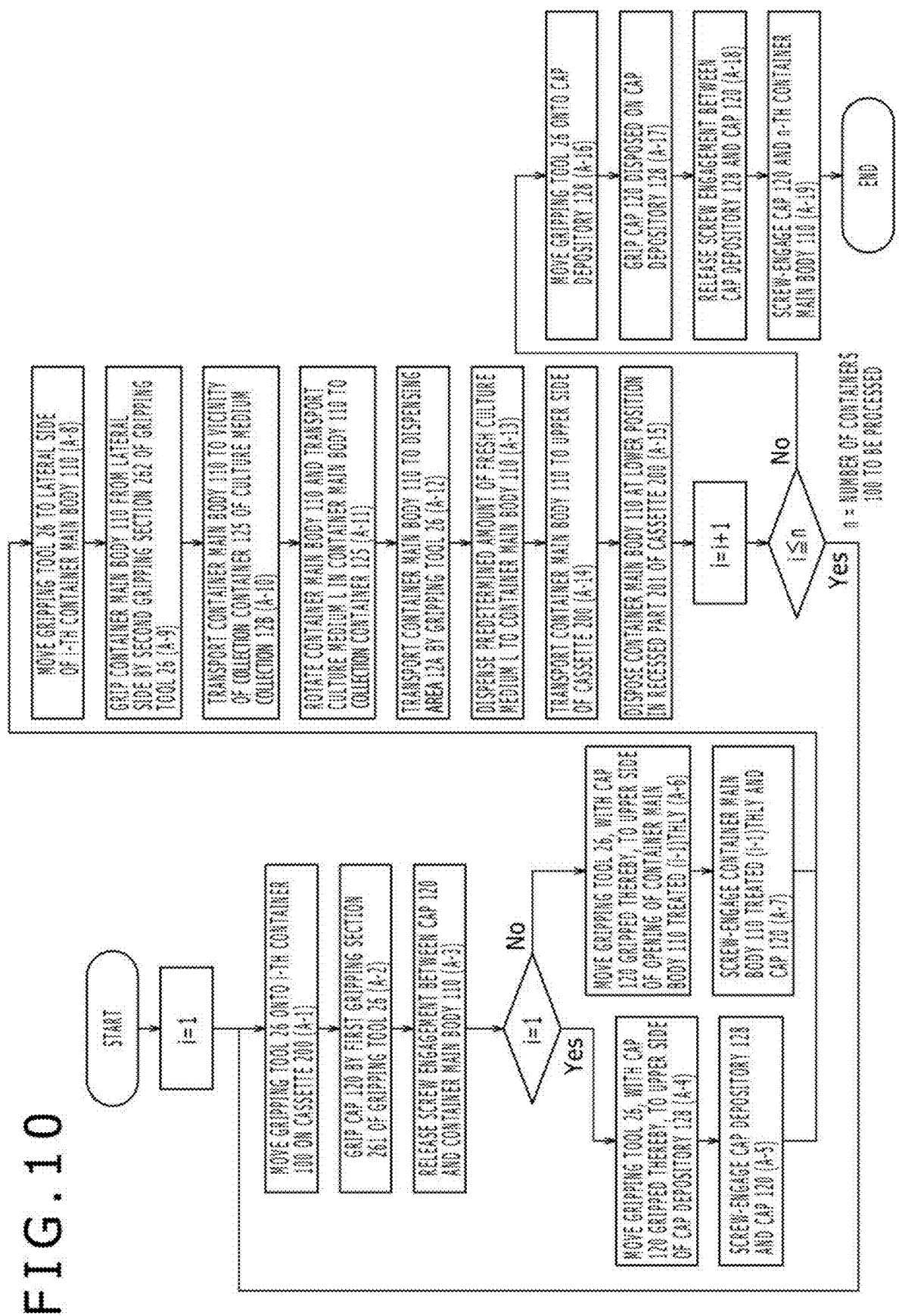
FIG. 10 is a flow chart for explaining the cell processing method according to the first embodiment of the present disclosure.

Note that the operation (S-6) of the robot 20 is performed along the flow chart shown in FIG. 10.

First, the cap 120 of the container 100 to be processed i-thly (initially, i=1) is detached from the container main body 110. Specifically, the gripping tool 26 is moved onto the container 100 to be processed on the cassette 200 by the robot (A-1). Next, the cap 120 is gripped by the first gripping section 264 of the gripping tool 26 (A-2). Subsequently, the cap 120 is rotated a predetermined number of times by rotating the gripping tool 26, to release the screw engagement between the cap 120 and the container main body 110 (A-3). Normally, the rotating direction is counterclockwise as the cap 120 is viewed from the gripping tool 26. In addition, the number of times of rotation is set at a number of times sufficient for releasing the screw engagement. Next, the cap 120 released from the screw engagement is lifted upward by the gripping tool 26. By this, the cap 120 is detached from the container main body 110.

Subsequently, the detached cap 120 is disposed at a predetermined position by the gripping tool 26.

Figure 11A:
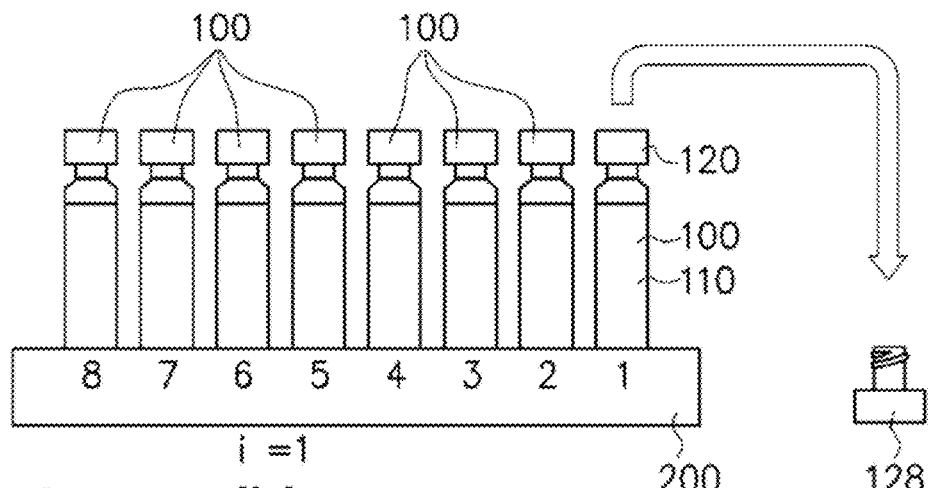
FIGS. 11(a)-11(c) show schematic views for illustrating the cell processing method according to the first embodiment of the present disclosure.

In the case where i=1, as shown in FIG. 11(a), the gripping tool 26 gripping the cap 120 is moved to an upper side of the cap depository 128 (A-4), and is rotated a predetermined number of times in a state wherein the cap depository 128 and the cap 120 are in contact with each other, to screw-engage the cap depository 128 and the cap 120 (A-5). Thereafter, the gripping of the cap 120 by the gripping tool 26 is released.

Figure 11B:
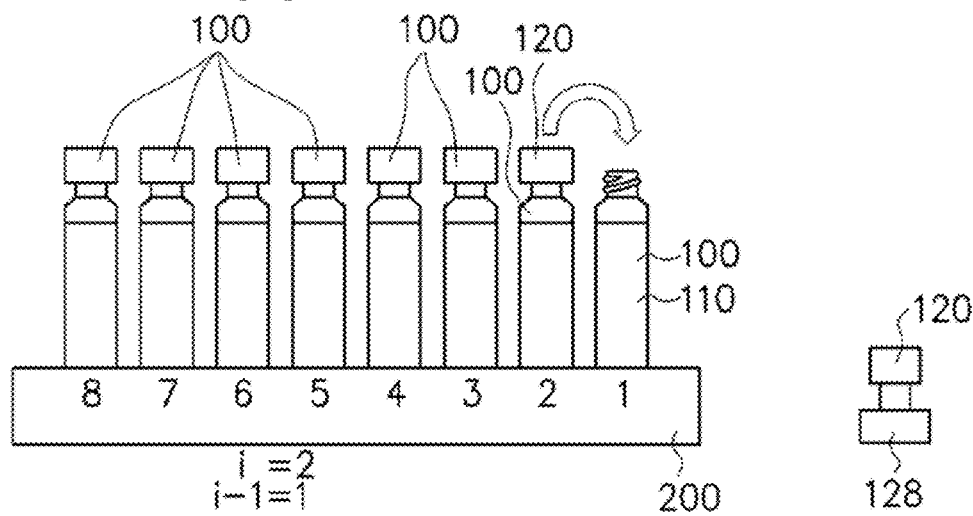
Figure 11C:
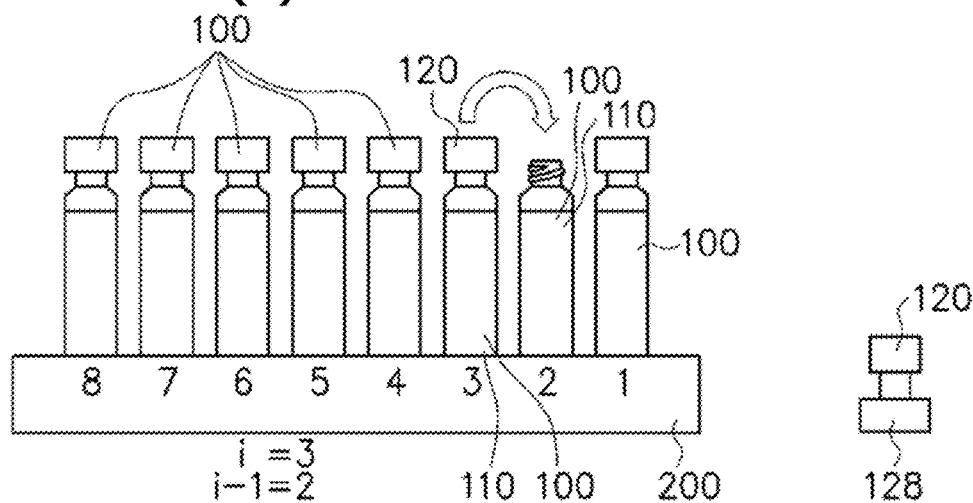

On the other hand, in accordance with an exemplary embodiment, in the case where i=2 or above, as illustrated in FIGS. 11(b) and 11(c), the detached cap 120 is attached to the container main body 110 processed (i−1)thly (step 2)). For example, in the case where i is 2, as shown in FIG. 11(b), the cap 120 of the container 100 to be processed secondly is attached to the container main body 110 processed firstly, and, as shown in FIG. 11(c), the cap 120 of the container 100 to be processed thirdly is attached to the container main body 110 processed secondly.

By this, an operation of detaching the cap 120 for processing and an operation of attaching the cap 120 after processing can be carried out simultaneously. Therefore, a process wherein an operation of temporarily disposing the cap 120 at the cap depository 128 upon detachment of the cap 120 and thereafter moving the cap 120 from the cap depository 128 to attach the cap 120 onto the container main body 110 is conducted at each occasion can be omitted.

Therefore, an operation path and an operation time required for detachment and attachment of the cap 120 can be shortened, and the time for which the inside surface of the cap 120 is exposed to the external environment is shortened, so that contamination can be prevented. As a result, overall reliability of the cell processing method using the cell processing system 1 can be enhanced.

Specifically, the gripping tool 26 gripping the cap 120 is moved to the upper side of the opening portion of the container main body 110 processed (i−1)thly (A-6), and is rotated a predetermined number of times in a state in which the opening portion and the cap 120 are in contact with each other to screw-engage the container main body 110 and the cap 120 with each other (A-7). Thereafter, the gripping of the cap 120 by the gripping tool 26 is released.

Next, in regard of the container 100 from which the cap 120 has been detached, processing is conducted (step 3)). In the present embodiment, the culture medium (liquid) L in the container main body 110 is disposed of, and a fresh culture medium is poured into the container 100, whereby the culture medium in the container 100 is exchanged.

In regard of the processing, first, the container main body 110 is gripped (step a)). Specifically, the gripping tool 26 is moved to a lateral side of the container main body 110 (A-8), and the container main body 110 is gripped from the lateral side by the second gripping section 262 of the gripping tool 26 (A-9). In accordance with an exemplary embodiment, the lateral sides of the container main body 110 are gripped by the gripping tool 26, whereby the robot 20 inclusive of the gripping tool 26 is prevented from passing over the opening of the container main body 110. In addition, also at the time of moving the gripping tool 26 to the lateral side of the container main body 110, it is preferable that the robot 20 inclusive of the gripping tool 26 does not pass over the opening of the container main body 110. As a result, dust or the like adhering to the robot 20 can be prevented from unintentionally dropping into the container main body 110.

Thereafter, the container main body 110 is transported into the vicinity of the collection container 125 in the processing area 12B which is the culture medium collection area (A-10).

Subsequently, the gripped container main body 110 is rotated, whereby the culture medium L in the container main body 110 is transported into the collection container 125 (step b) and A-11). In the present embodiment, as depicted in FIGS. 12(a) to 12(g), the rotation of the container main body 110 is conducted by rotating the container main body 110 about a center axis consisting of an axis parallel to the axis of rotation of the gripping tool 26, in the same direction.

In general, in the case of transporting the culture medium L from the container main body 110 into the collection container 125 by manual operation, as shown in FIGS. 13(a) to 13(e), upon discharging the culture medium L by once tilting the container main body 110 the container main body 110 is usually turned back (FIG. 13(d)) in a direction opposite to the tilting direction, whereby the opening 111 of the container main body 110 is oriented vertically upward. In this case, the culture medium L is liable to remain in the vicinity of a lower side toward which the opening 111 of the container main body 110 is tilted, and dripping of the culture medium L from the opening 111 of the container main body 110 to the outside of the opening 111, namely, so-called liquid dripping may occur (FIG. 13(e)). In such a case, contamination of the inside of the container main body 110 starting from the culture medium L flowing out due to the liquid dripping tends to occur.

On the other hand, in the present embodiment, the culture medium L remaining in the vicinity of the lower side toward which the opening 111 is once tilted is located in the vicinity of the upper side of the opening 111, since the container main body 110 is rotated in the same direction and the opening 111 is thereby reversed downside up (FIGS. 12(e) and 12(f)). By this, a situation wherein the culture medium L is transported to an outer peripheral wall surface of the opening 111 to cause liquid dripping can be prevented (FIG. 12(g)).

Note that while the container main body 110 is configured such as to be rotated about a center axis consisting of an axis parallel to the axis of rotation of the gripping tool 26 by the robot 20, with such an axis serving as the center axis, 360° rotation of the container main body 110 in the same direction by the robot 20 is possible.

In addition, the rotation of the container main body 110 may be performed while being accompanied by a translational motion. By this, the opening 111 of the container main body 110 can be disposed in the vicinity of the opening of the collection container 125, so that the culture medium L is transported into the collection container 125 more easily and reliably.

Further, at the time when the container main body 110 has been rotated and the opening 111 is oriented toward the vicinity of a vertically lower direction, the container main body 110 is preferably reciprocated up and down. With such an operation, the culture medium L can be transported from the container main body 110 into the collection container 125 more reliably.

In addition, the sensor 126 present on a lower side of the collection container 125 can measure the amount of the culture medium L collected. Therefore, such problems as whether or not the culture medium L has been transported properly or whether there is abnormality in a cell culture in the container main body 110 can be surmised based on the amount of the culture medium L.

Note that in the present embodiment, in the aforesaid processing for disposing of the culture medium, namely, in steps a) and b), the robot 20 is operated in such a manner as not to pass over a vertical line of the opening of the collection container 125. By this, foreign matters such as dusts and abrasion debris adhering to the robot 20 are prevented from mixing into the collection container 125. In analyzing the culture medium in the collection container 125 including analyzing whether the cell culturing in the container 100 has been performed normally, the presence of such foreign matter may hamper the analysis. In the present embodiment, mixing of such foreign matter can be prevented, and whereby the cell processing system 1 and the cell processing method can be enhanced in reliability.

After the culture medium L is transported from the container main body 110 into the collection container 125 as above, a fresh culture medium L is dispensed into the container main body 110. Specifically, first, while the container main body 110 is kept gripped by the gripping tool 26, it is transported to the processing area 12A which is a dispensing area (A-12). Next, the dispensing pump 121 is operated to dispense a predetermined amount of the fresh culture medium L into the container main body 110 through the tube 123 (A-13). Note that the dispensing amount is being measured by the liquid measurement sensor 124 with the lapse of time, whereby the final dispensing amount is controlled.

Figure 14:
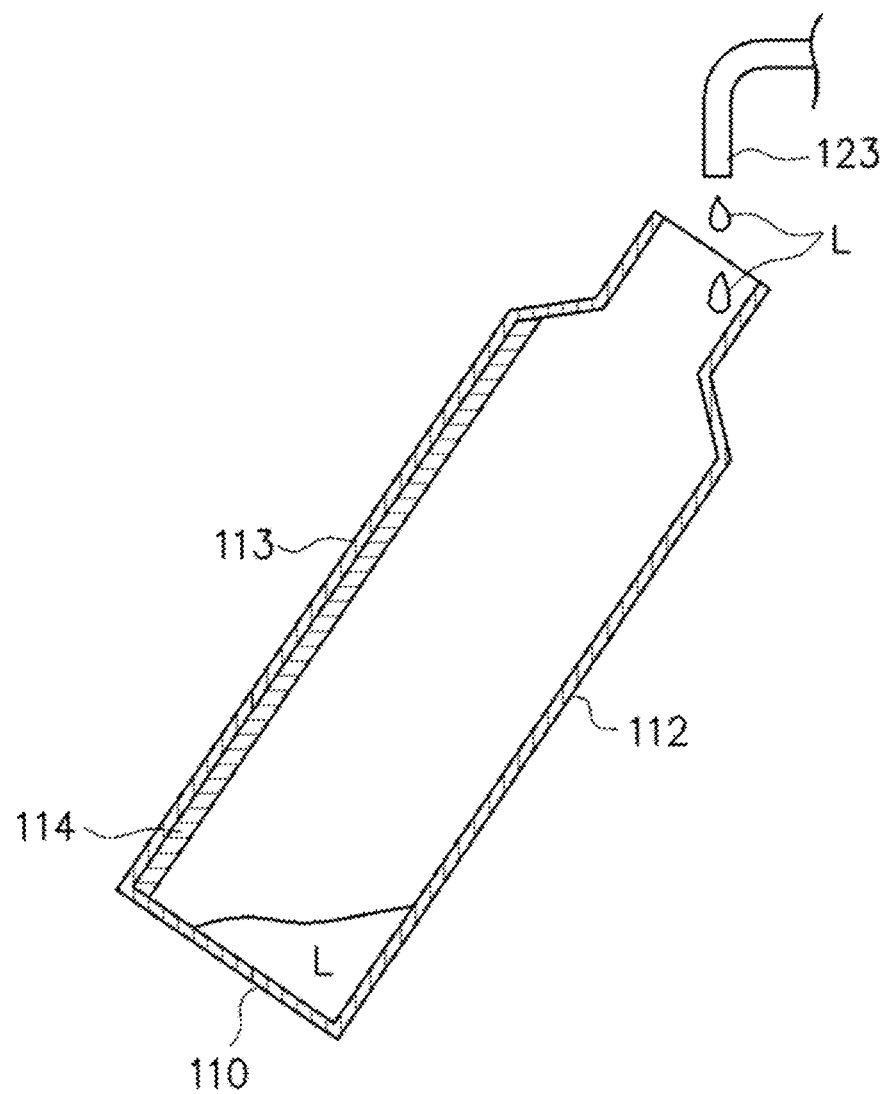
FIG. 14 is a schematic view for illustrating the cell processing method according to the first embodiment of the present disclosure.

In accordance with an exemplary embodiment, it can be preferable to perform the dispensing in such a manner that the culture medium L supplied through the tube 123 does not make direct contact with the cell culture 114 in the container main body 110. For example, in the case where the cell culture 114 is cultured on and adhering to a main surface 113 on one side of the container main body 110 as shown in FIG. 14, it is preferable to supply the culture medium L from the opening 111 in a state in which the container main body 110 is tilted such that the main surface 113 is located on the upper side and a main surface 112 is located on the lower side. By this, unintentional damage to or dissection of the cell culture 114 can be prevented.

Next, the container main body 110 is transported to the upper side of the cassette 200 (A-14), and is thereafter disposed at a lower position in the recessed part 201 of the cassette 200 (A-15).

The above steps A-1 to A-13 are repeated until i increases from 1 to n which is the number of the containers 100, whereby exchange of the culture medium L in each of the containers 100 can be performed automatically.

In accordance with an exemplary embodiment, as soon as the container main body 110 with the fresh culture medium L once dispensed thereinto is disposed in the recessed part 201, the cap 120 of the container 100 to be processed next is attached to the container main body 110 (A-7).

In addition, in the case where there is no container 100 to be processed next, namely, in regard of the container 100 to be processed n-thly, the cap 120 disposed on the cap depository 128 is attached thereto.

Specifically, the gripping tool 26 is moved onto the cap depository 128 (A-16), and the cap 120 disposed on the cap depository 128 is gripped by the second gripping section 264 of the gripping tool 26 (A-17). Next, the cap 120 is rotated by rotating the gripping tool 26, to release the screw engagement between the cap depository 128 and the cap 120 (A-18). Subsequently, the cap 120 is disposed on the container main body 110, and the gripping tool 26 is rotated together with the cap 120 in a state where the cap 120 is in contact with the opening 111 of the container main body 110, to screw-engage the cap 120 and the container main body 110 (A-19).

In accordance with an exemplary embodiment, the aforementioned automatic operation conducted using the robot 20 is configured such that under a predetermined condition, for example, in the case where the processing has been finished for all the containers 100 on the cassette 200, in the case where the culture medium in an amount of not less than a predetermined amount has been transported into the collection container 125, in the case where the amount of the culture medium L in the culture medium storage container 122 has decreased to or below a predetermined amount, or in the case where other unexpected phenomenon is generated, the automatic operation is stopped, whereas in the case where such a condition is not generated, the automatic operation is continued (S-7).

In this case, the operator, for example, first checks whether or not the processing for all the containers 100 on the cassette 200 has been finished, and whether or not there is any other container 100 to be processed that is not on the cell processing system 1 (S-8).

In the case where a container 100 to be processed is present, it is next checked whether or not the culture medium L is present in the culture medium storage container 122 (S-9), and, if the culture medium L is not present, the culture medium L is added to the culture medium storage container 122, or the culture medium storage container 122 is replaced by one filled with a new culture medium L (S-10).

Next, it is checked whether or not a predetermined amount of the culture medium L is present in the collection container 125 (S-11), and, if the predetermined amount of the culture medium L is present, the culture medium L is transferred into other container and disposed of, or the collection container 125 is replaced by a new collection container 125 (S-12).

Subsequently, the cassette 200 is collected, the containers 100 having undergone the processing are collected, the remaining containers 100 are added to the cassette 200, and the aforesaid step S-4 is carried out.

In addition, in the case where in step S-7 there is no container 100 to be processed, the instruments and materials for performing dispensing are detached and removed in the processing area 12A (S-13), disposal of the collected culture medium L and removal of instruments and materials are conducted in the processing area 12B (S-14), and removal of the cassette 200 is conducted in the processing area 12C (S-15).

Thereafter, the power source for the cell processing system 1 is turned OFF, and the operations are finished (S-16).

Thus, by the method according to the present embodiment, processing of cells can be performed relatively efficiently.

Particularly, for example, in the culture medium disposal treatment, the robot 20 is configured to operate in such a manner as not to pass over the vertical line of the opening of the collection container 125, whereby analysis of the collected culture medium L is facilitated, and reliability of the cell processing can be enhanced.

In addition, especially, the operation of detaching the cap 120 for performing processing and the operation of attaching the cap 120 after the processing are conducted simultaneously, whereby the operation path and operation time required for the detachment and attachment of the cap 120 can be shortened, and the time for which the inside surface of the cap 120 is exposed to the exterior environment is shortened, so that contamination can be prevented. As a result, total reliability of the cell processing method conducted using the cell processing system 1 can be enhanced.

A second embodiment of the present disclosure will be described below.

Figure 15:
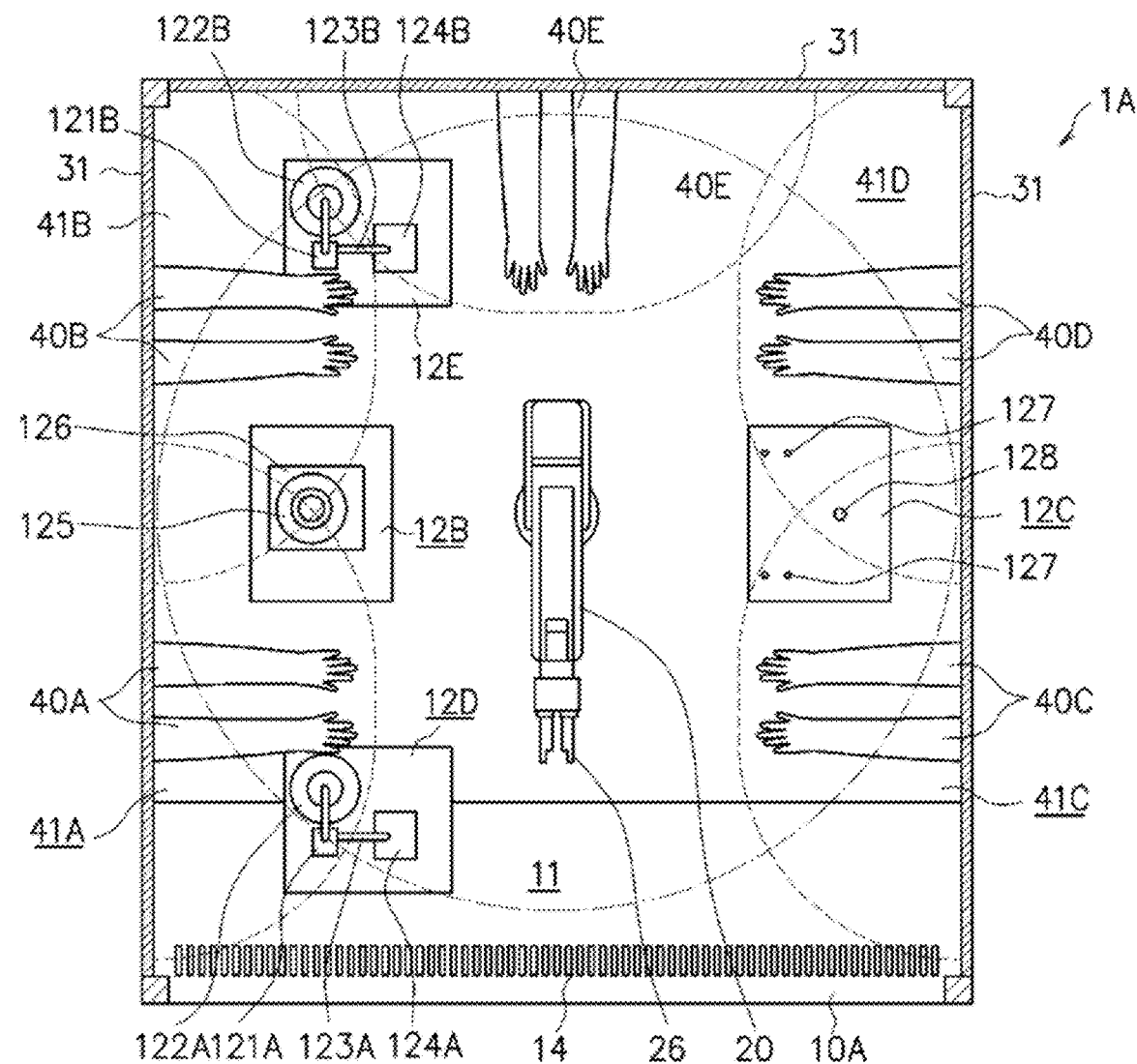
FIG. 15 is a sectional view of a cell processing system according to a second embodiment of the present disclosure.

FIG. 15 is a sectional view of a cell processing system according to the second embodiment of the present disclosure. Note that in the figure the same configurations as those in the cell processing system 1 are denoted by the same reference symbols as used above.

Hereinafter, differences between the present embodiment and the first embodiment will be described in detail, and, in regard of similar items, descriptions thereof will be omitted.

A cell processing system 1A according to the present embodiment illustrated in FIG. 15 differs from the cell processing system 1 according to the first embodiment, mainly in that it is a system for dissection of a cell culture cultured in a container 100.

A base 10A in the present embodiment is provided with a processing area 12D for dispensing a buffer, in place of and at similar position to the processing area 12A which is the culture medium dispensing area, and with a processing area 12E for dispensing a cell dissociation agent, on the depth side as viewed from the carrying-in/carrying-out area 11 on the base 10A.

Dispensing pumps 121A and 121B, storage containers 122A and 122B, tubes 123A and 123B, and liquid measurement sensors 124A and 124B are disposed in the processing areas 12D and 12E, respectively. The dispensing pumps 121A and 121B, the storage containers 122A and 122B, the tubes 123A and 123B, and the liquid measurement sensors 124A and 124B have configuration similar to that of the dispensing pump 121, the culture medium storage container 122, the tube 123, and the liquid measurement sensor 124 except for differences in the liquid used.

The buffer dispensed in the processing area 12D is not particularly limited, and examples thereof include acetate buffer, phosphate buffer, citrate buffer, borate buffer, tartrate buffer, TRIS buffer, and phosphate buffered physiological saline solution.

In addition, the cell dissociation agent dispensed in the processing area 12E is not particularly limited, and examples thereof include collagenase, trypsin, dispase, ethylenediaminetetraacetic acid (EDTA), and Accutase. In addition, the cell dissociation agent may be a liquid composition in which these components are dissolved or dispersed.

In addition, a working section 40E is disposed in the center on the side opposite to the carrying-in/carrying-out area 11, namely, at a side wall in the center of the depth side as viewed from the carrying-in/carrying-out area 11, on the base 10A.

The working section 40E has its working area 41E individually overlapping with a working area 41B of a working section 40B and a working area 41D of a working section 40D. By this, things for use in processing can be moved between the working section 40E and the working sections 40A and 40B. Therefore, things for use in processing can be accepted from the carrying-in/carrying-out area 11 through the working sections 40A and 40B or through the working sections 40C and 40D. In addition, things received from the working section 40B or 40D can be transferred to the working section 40D or 40B.

In addition, the working sections 40B and 40E have their working areas 41B and 41E overlapping with the processing area 12E, so that operations in the processing area 12E can be performed there. Therefore, in such a cell processing system 1A, operations in the processing area 12D can be performed from the carrying-in/carrying-out area 11 or by use of the working section 40A, whereas operations in the processing area 12E can be performed by use of the working section 40B or the working section 40E.

Now, a cell processing method in the present embodiment conducted using the aforementioned cell processing system 1A will be described below. Note that when the method in the present embodiment is compared to the method in the first embodiment, processing in the processing area 12A is replaced by processing in the processing areas 12D and 12E. Therefore, the following description will be focused on this point, and descriptions of similar items as above will be omitted.

As aforementioned, the cell processing system 1A has the processing areas 12D and 12E in place of the processing area 12A; therefore, in place of the operation in the processing area 12A in step S-2 in the above-described first embodiment, instruments and materials for dispensing a buffer and a cell dissociation agent are disposed and prepared in the processing areas 12D and 12E. In addition, similarly, in place of the operation in the processing area 12A in steps S-9 and S-10 in the above-described first embodiment, the buffer and the cell dissociation agent are added, if necessary, in the processing areas 12D and 12E. In addition, in place of the operation in the processing area 12A in step S-13 in the above-described first embodiment, instruments and materials for dispensing the buffer and the cell dissociation agent are detached and removed in the processing areas 12D and 12E.

In addition, an automatic operation by the cell processing system 1A is carried out according to the following procedure.

First, by operations similar to those in steps A-1 to A-7 in the first embodiment, the cap of the container 100 is detached.

Next, by operations similar to those in steps A-8 to A-11 in the first embodiment, the culture medium L present in the container main body 110 is transported into the collection container 125.

Subsequently, in the processing area 12D, the buffer is dispensed into the container main body 110. In accordance with an exemplary embodiment, this operation can be carried out similar to that in steps A-12 and A-13 in the first embodiment.

Next, using the dispensed buffer, a cell culture 114 present in the container main body 110 is rinsed. This operation can be carried out using the gripping tool 26, specifically by rotating the container main body 110 such that a main surface 113 of the container main body 110 is located on the lower side, and thereafter vibrating (reciprocating) the container main body 110 horizontally.

Subsequently, by operations similar to those in steps A-8 to A-11 in the first embodiment, the buffer (the rinse liquid after the rinsing) present in the container main body 110 is transported into the collection container 125.

Next, in the processing area 12E, the cell dissociation agent is dispensed into the container main body 110. This operation can be carried out in similar to that in steps A-12 and A-13 in the first embodiment.

Subsequently, by operations similar to those in steps A-14 and A-15 in the first embodiment, the container 100 is disposed on the cassette 200.

The above operations are repeated to finish processing for all the containers 100, after which the cap is attached to the finally processed container main body 110 by operations similar to those in steps A-16 to A-19.

The other operations can be performed similar to those in the aforementioned method of the first embodiment.

In addition, each of the containers 100 having undergone the aforesaid processing can be put to a cell dissociation reaction by the operator.

By the cell processing system and method according to the present embodiment as above, also, effects similar to those of the first embodiment can be obtained.

A third embodiment of the present disclosure will be described below.

Figure 16:
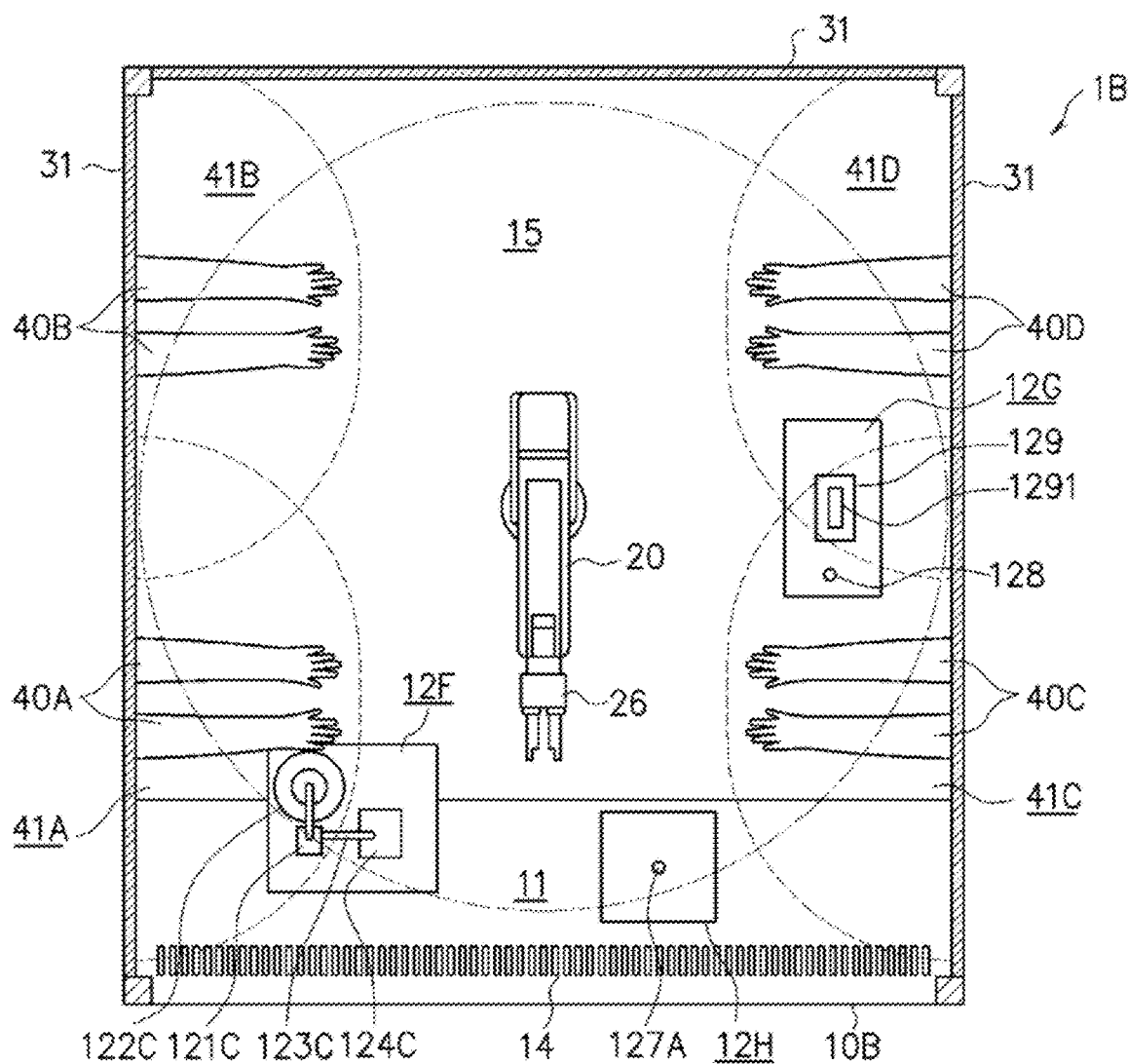
FIG. 16 is a sectional view of a cell processing system according to a third embodiment of the present disclosure.
Figure 17:
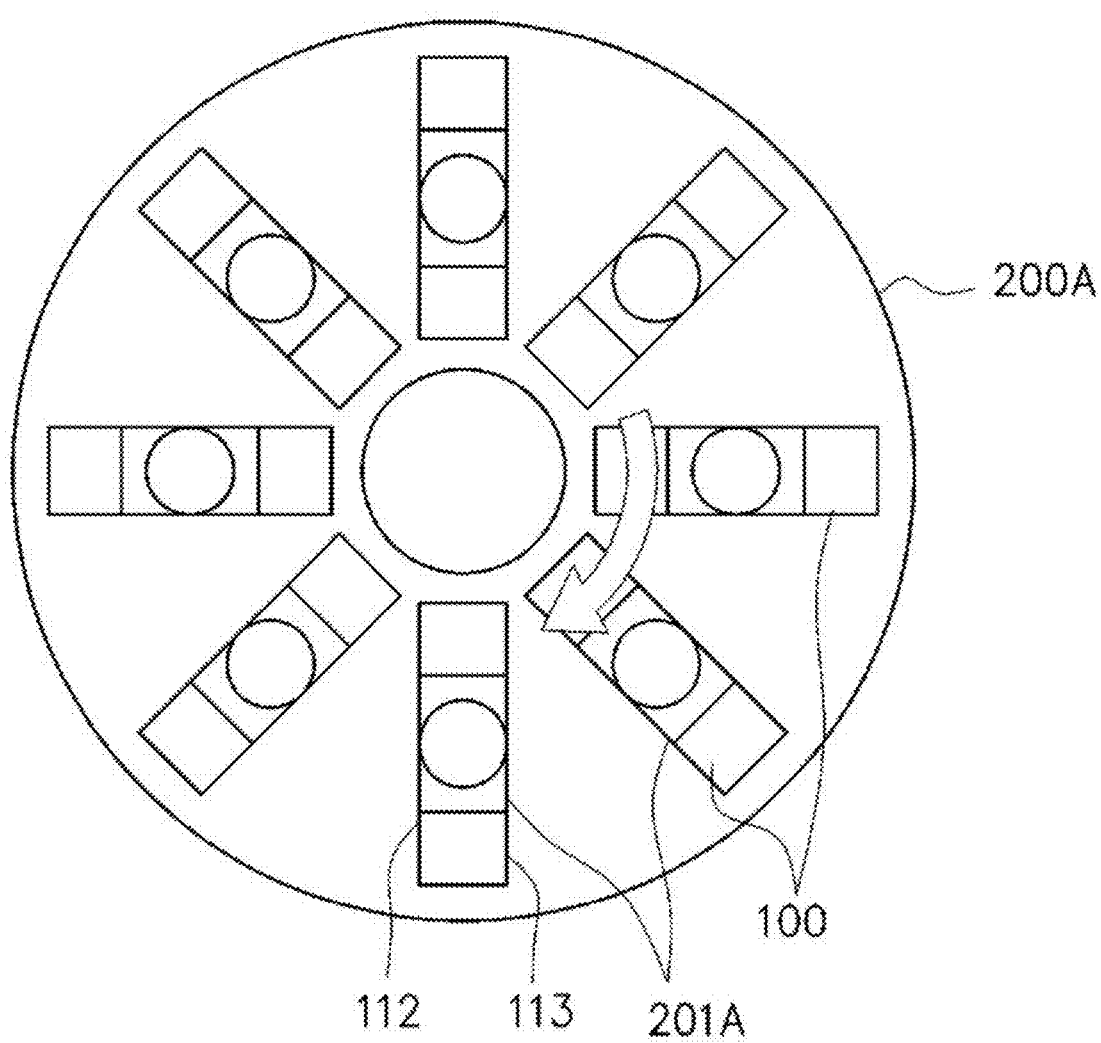
FIG. 17 is a schematic view showing an example of a cassette for containers for use in the cell processing system shown in FIG. 16.

FIG. 16 is a sectional view of a cell processing system according to a third embodiment of the present disclosure, and FIG. 17 is a schematic view showing an example of a cassette for containers for use in the cell processing system shown in FIG. 16. Note that in the figures the same configurations as those in the cell processing system 1 are denoted by the same reference symbols as used above.

Hereinafter differences of the present embodiment from the first embodiment will be described in detail below, and descriptions of similar items as above will be omitted.

A cell processing system 1B according to the present embodiment illustrated in FIG. 16 differs from the cell processing system 1 of the first embodiment mainly in that it is a system for inoculating cells in the container 100.

A base 10B in the present embodiment has a configuration wherein a processing area 12F for inoculation of cells is disposed in place of and at similar position to the processing area 12A which is a culture medium dispensing area, a processing area 12G for attachment and detachment of a cap is disposed at similar position to the processing area 12C, a processing area 12H as a depository of the container 100 is disposed in the carrying-in/carrying-out area 11, and, on the other hand, the processing area 12B as a culture medium collection area is omitted.

In the processing area 12F, there are disposed a dispensing pump 121C, a storage container 122C, a tube 123C, and a liquid measurement sensor 124C. The dispensing pump 121C, the storage container 122C, the tube 123C, and the liquid measurement sensor 124C have configuration similar to that of the dispensing pump 121, the culture medium storage container 122, the tube 123, and the liquid measurement sensor 124 except for differences in the liquid to be used.

The liquid to be dispensed in the processing area 12F is not particularly limited so as long it includes cells, and may be, for example, a dispersion including the above-mentioned cells dispersed in a liquid such as a culture medium or a buffer.

In addition, in the processing area 12G, there is provided a securing base 129 in addition to the cap depository 128. The securing base 129 is a base for securing the container main body 110, and is provided with a securing hole 1291 which is a recessed part corresponding to a bottom surface of the container main body 110. A configuration is adopted wherein when the container main body 110 is disposed in the securing hole 1291, the opening 111 of the container main body 110 is oriented vertically upward, and at the time of rotating the cap 120 by the gripping tool 26, the securing hole 1291 secures the container main body 110 to the securing base 129 such as to prevent the container main body 110 from rotating.

In the processing area 12H, a securing pin 127A is disposed. The securing pin 127A is configured to be rotatable, and can be engaged with a cassette 200A. The securing pin 127A can be rotated together with the cassette 200A in accordance with an operation of the robot 20, by a driving mechanism disposed in the base 10B.

As shown in FIG. 17, the cassette 200A is circular disc-like in shape, and is provided on the backside in the center with a hole, which can be engaged with the securing pin 127A. In addition, the cassette 200A is formed with a plurality of recessed parts 201A arranged radially. The recessed parts 201A are each shaped correspondingly to the bottom surface of the container 100, and are configured such that the container main bodies 110 are disposed with their long axes arranged radially in relation to the cassette 200A in plan view.

By such configurations of the processing area 12H and the cassette 200A, the container 100 for use in processing can be appropriately moved to a place near the robot 20. Therefore, operations of the robot 20 can be simplified, and the processing is enhanced in efficiency.

Now, a cell processing method of the present embodiment conducted using the aforementioned cell processing system 1B will be described below. Note that the following description is focused on differences between the method of the present embodiment and the method of the first embodiment, and descriptions of similar items as above will be omitted.

First, by operations similar to those in the aforementioned first embodiment, instruments and materials necessary for inoculation of cells are disposed and prepared in the processing areas 12F and 12H.

In addition, an automatic operation by the cell processing system 1B is carried out according to the following procedure.

First, the cap of the container 100 is detached. In regard of this, first, the container 100 is gripped from a lateral side of the container main body 110 disposed on the cassette 200, by second gripping section 262 of the gripping tool 26.

Next, the gripped container 100 is disposed in the securing hole 1291 of the securing base 129 in the processing area 12G.

Subsequently, similarly in steps A-1 to A-7 described above, the cap 120 of the container 100 disposed on the securing base 129 is detached, and is disposed in a predetermined place.

Next, similarly in steps A-8 and A-9, the container main body 110 is gripped, and the container main body 110 is transported to the processing area 12F for inoculation of cells.

Subsequently, the dispensing pump 121C is operated, to dispense a predetermined amount of a cell-containing liquid into the container main body 110 through the tube 123C.

Thereafter, similarly in steps A-14 and A-15, the container main body 110 is disposed in the recessed part 201A of the cassette 200A.

The above operations are repeated to finish processing for all the containers 100, after which, in operations similar to those in steps A-16 to A-19, the cap is attached to the finally processed container main body 110.

The other operations can be carried out similar to those in the method of the first embodiment described above.

By the cell processing system and method according to the present embodiment as above, also, effects similar to those of the first embodiment can be obtained.

Figure 18:
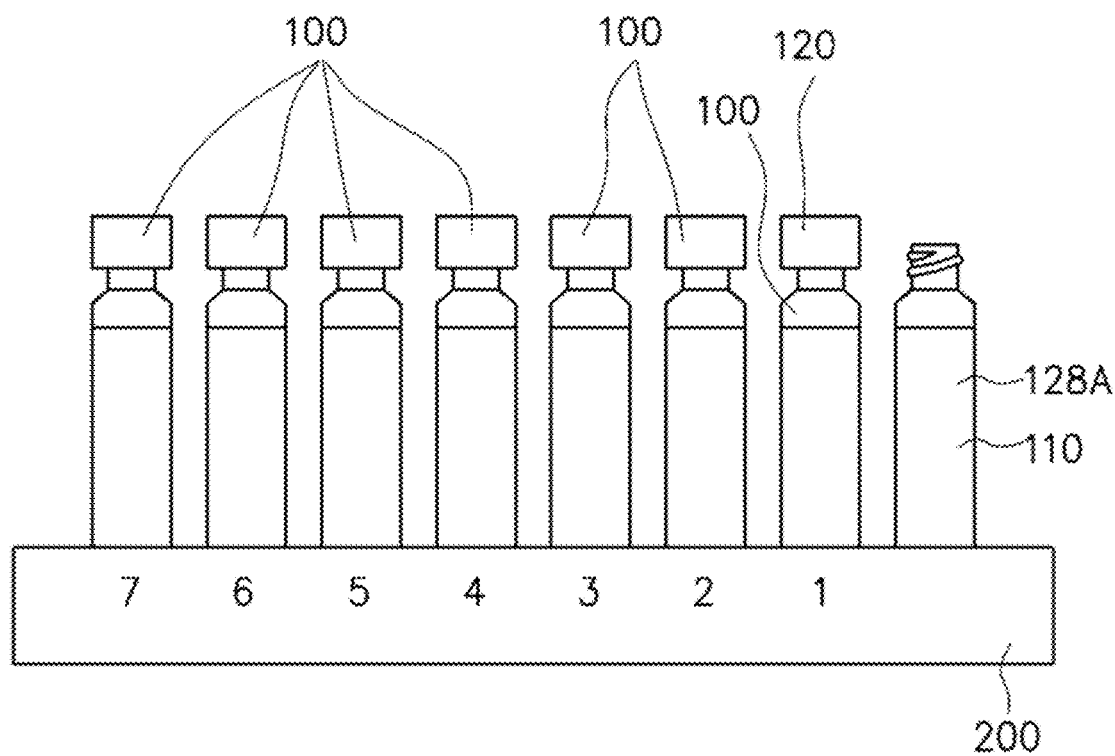
FIG. 18 is a schematic view showing another modification of the present disclosure.

Note that as a modification of the aforementioned first to third embodiments, there can be mentioned, for example, an example wherein as shown in FIG. 18 the same container main body 110 as the container main body 110 of other container 100 is used as the cap depository 128A, and the cap depository disposed on the base is omitted. In such a case, even in the case where the shape of the container 100 is changed, the cap depository can be easily prepared by utilizing the container 100 of the same kind. In other words, the cell processing system can be utilized, regardless of the shape of the container 100.

In addition, as another modification, there can be mentioned as the gripping tool, one on which a force sense sensor is mounted. In such a case, since the weight of the container can be sensed, the dispensing amount can be measured by the force sense sensor, even without using such a sensor as a weight sensor as an instrument for dispensing. In other words, a sensor can be omitted in the processing area for dispensing. In addition, where a force sense sensor is adopted, it is thereby possible, for example, to determine whether or not the gripping tool has made contact with the container. As a result, it is possible, for example, to check whether the gripping tool has made contact with the container, to dispose the gripping tool in a position suitable for gripping, and to ensure more reliable gripping.

In addition, while the gripping tool has been described as a parallel gripper in each of the aforementioned embodiments, there can be used various grippers such as a rotary gripper, a one-side movable gripper, and a both-side movable gripper.

In addition, the shape of the gripping tool can be changed appropriately.

Figure 19:
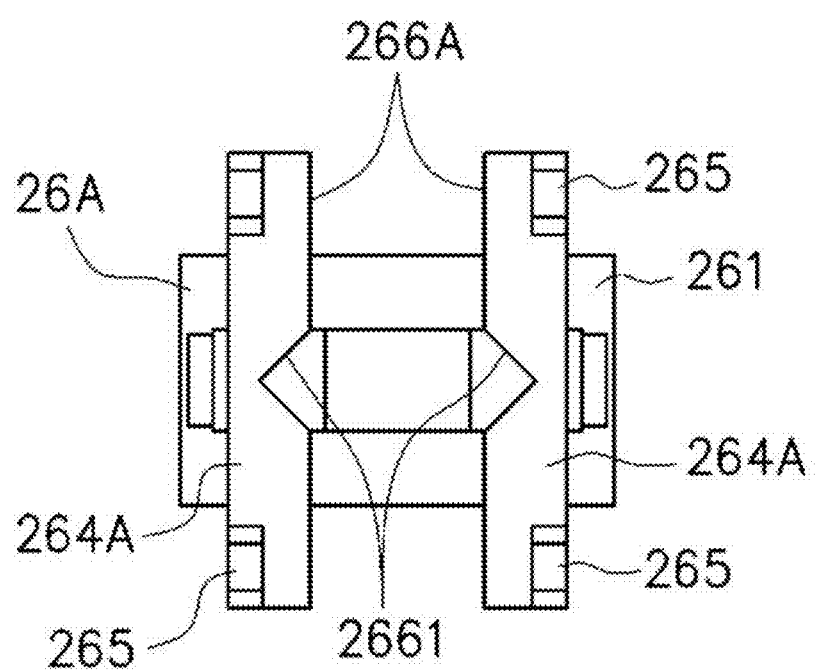
FIG. 19 is a schematic view showing a further modification of the present disclosure.

For instance, in a gripping tool 26A depicted in FIG. 19, in the vicinity of the center of gripping surfaces 266A of first gripping section 264A, recessed parts 2661 are disposed along an axial direction. The recessed parts 2661 are v-shaped in sectional shape, whereby the area of contact between the first gripping section 264A and the cap 120 is increased when the cap 120 is gripped by the first gripping section 264A. Therefore, the cap 120 can be held by the first gripping section 264A more securely, and, even in the case of rotating the cap 120 by the first gripping section 264A, a rotating force can be transmitted from the first gripping section 264A to the cap 120 more reliably.

In addition, for example, the second gripping section of the gripping tool may be provided on only one-side end portions of the first gripping section.

In addition, in preparing and removing instruments and materials in each of the processing areas by the operator, the order of operations can be changed appropriately. Therefore, for example, in respective ones of steps S-2 to S-4, steps S-9 to S-12, and steps S-13 to S-15 in the cell processing method according to the first embodiment, the order of each of the steps can be changed.

While the present disclosure has been described above referring to the embodiments illustrated in the drawings, the present disclosure is not limited to the embodiments.

In the present disclosure, each of the configurations can be replaced by any one that can exhibit an equivalent function, or arbitrary configurations may be added.

The detailed description above describes a liquid transport method, a cell processing system, and a cell processing method. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A liquid transport method in processing of cells, the liquid transport method comprising:
    a) a step in which lateral sides of a container holding a liquid is gripped by a gripping tool of a robot from a cassette configured to hold a plurality of containers, the cassette having a plurality of recessed parts each shaped corresponding to a bottom surface of the container, the gripping of the container being conducted in such a manner that the gripping tool is not present over a vertical line of an opening of the container;
    b) a step in which the liquid in the container is transported into a collection container by rotating the gripped container and orienting the opening of the gripped container toward a vertically lower direction;
    wherein in steps a) and b), the robot operates in such a manner as not to pass over a vertical line of an opening of the collection container; and
    wherein the container has a container main body and a cap, the method further comprising:
        detaching the cap of the container from the container main body by the robot and disposing the cap on a cap depository prior to conducting the step a); and
        gripping the lateral sides of the container main body of the container.

2. The liquid transport method according to claim 1,
    wherein the gripping tool is rotatable, and
    in step b), the container is rotated, in the same direction, about a center axis consisting of an axis parallel to an axis of rotation of the gripping tool.

3. The liquid transport method according to claim 1,
    wherein in step b), the container is reciprocated up and down when the opening of the container is oriented downward.

4. The liquid transport method according to claim 1, wherein in step b), the rotation of the container is performed while being accompanied by a translational motion.

5. The liquid transport method according to claim 1, wherein the liquid is a culture medium.

6. A cell processing system, which is a system for use in processing of cells by use of a container, the cell processing system comprising:
   a rectangular base provided with a plurality of processing areas for performing processing by use of the container and a carrying-in/carrying-out area where things for use in the processing can be carried in and carried out;
   a robot that is provided on the base and has a gripping tool capable of gripping at least part of the container, the robot being adjacent to each of the plurality of processing areas;
   a housing that covers the processing areas, the robot, and at least part of the carrying-in/carrying-out area and is able to maintain cleanliness of an inside of the housing;
   at least one working section that is disposed on the housing or the base and is configured in such a manner that manual operation in the housing from outside of the housing;
   wherein the gripping tool of the robot can reach each of the processing areas;
   the housing is configured such that a part of the housing adjacent to the carrying-in/carrying-out area can be opened and closed;
   the at least one working section is configured such that a workable area of the at least one working section overlaps with the processing area and/or the carrying-in/carrying-out area for use in the processing can be moved between the respective processing areas and the carrying-in/carrying-out area through the at least one working section;
   at least one openable and closeable slide shutter, the at least one openable and closeable shutter configured to produce a closed system when the at least one shutter is closed;
   a plurality of suction portions in the base and in a vicinity of the at least one shutter, the plurality of suction portions configured to generate a clean space having a reduced-pressure state in the clean space; and
   wherein the plurality of processing areas comprise:
      a first processing area configured to dispense a liquid into the container;
      a second processing area configured to dispose of and collect a culture medium in the container; and
      a third processing area configured to attach and detach a cap of the container.

7. The cell processing system according to claim 6, further comprising:
   a plurality of the working sections, wherein workable areas of the working sections adjacent to each other overlap with each other.

8. The cell processing system according to claim 6, wherein manual preparation for the processing in the processing area can be performed by the working section.

9. The cell processing system according to claim 6, wherein the processing is performed by the robot.

10. The cell processing system according to claim 6, wherein the working section is a glove.

11. The cell processing system according to claim 6, wherein the liquid is a culture medium.

12. The cell processing system according to claim 6, wherein the first processing area includes a dispensing pump, a culture medium storage container for storing a culture medium, a tube for supplying the culture medium from the culture medium storage container into the container by the dispensing pump, and a liquid measurement sensor for measuring the amount of the liquid dispensed into the container.

13. The cell processing system according to claim 6, wherein the second processing area includes a collection container configured to collect the culture medium transported from the container and a sensor configured to measure an amount of the collected culture medium.

14. The cell processing system according to claim 13, wherein the sensor is a weight sensor disposed under the collection container or an optical sensor configured to optically detect an amount of liquid.

15. The cell processing system according to claim 14, wherein the third processing area includes a securing means for securing a cassette for the container, the container being one of a plurality of containers and a cap depository for supporting the cap detached from the container.

16. A cell processing system, which is a system for use in processing of cells by use of a container, the cell processing system comprising:
   a rectangular base provided with a plurality of processing areas for performing processing by use of the container and a carrying-in/carrying-out area where things for use in the processing can be carried in and carried out, the plurality of processing areas including a first processing area configured to dispense a liquid into the container, a second processing area configured to dispose of and collect a culture medium in the container, and a third processing area configured to attach and detach a cap of the container;
   a robot that is provided on the base and has a gripping tool capable of gripping at least part of the container, the robot being adjacent to each of the plurality of processing areas;
   a housing that covers the processing areas, the robot, and at least part of the carrying-in/carrying-out area and is able to maintain cleanliness of an inside of the housing;
   a plurality of working sections disposed on the housing or the base and configured in such a manner that manual operation in the housing from outside of the housing can be performed;
   wherein the gripping tool of the robot can reach each of the processing areas;
   the housing is configured such that a part of the housing adjacent to the carrying-in/carrying-out area can be opened and closed; and
   the plurality of working sections include at least two working sections on one side of the rectangular base and at least two working sections on an opposite side of the rectangular base, the plurality of working sections being configured such that a workable area of the plurality of working sections overlaps with the processing area and/or the carrying-in/carrying-out area for use in the processing can be moved between the respective processing areas and the carrying-in/carrying-out area through the plurality of working sections.

* * * * *